US012296354B2

(12) United States Patent
Inoue et al.

(10) Patent No.: US 12,296,354 B2
(45) Date of Patent: May 13, 2025

(54) FINE WATER DISCHARGE DEVICE

(71) Applicant: AISIN CORPORATION, Aichi (JP)

(72) Inventors: Shinsuke Inoue, Kariya (JP); Akiyoshi Hirano, Kariya (JP); Akira Yamaguro, Kariya (JP); Yoko Adachi, Kariya (JP); Machiyo Yasuda, Kariya (JP)

(73) Assignee: AISIN CORPORATION, Aichi (JP)

( * ) Notice: Subject to any disclaimer, the term of this patent is extended or adjusted under 35 U.S.C. 154(b) by 730 days.

(21) Appl. No.: 17/269,387

(22) PCT Filed: Feb. 27, 2019

(86) PCT No.: PCT/JP2019/007674
§ 371 (c)(1),
(2) Date: Feb. 18, 2021

(87) PCT Pub. No.: WO2020/054100
PCT Pub. Date: Mar. 19, 2020

(65) Prior Publication Data

US 2021/0170431 A1 Jun. 10, 2021

(30) Foreign Application Priority Data

Sep. 14, 2018 (JP) ................................ 2018-172166

(51) Int. Cl.
*B05B 7/24* (2006.01)
*A61M 11/00* (2006.01)
(Continued)

(52) U.S. Cl.
CPC .......... *B05B 7/2491* (2013.01); *B05B 7/0081* (2013.01); *B05B 7/22* (2013.01);
(Continued)

(58) Field of Classification Search
CPC ....... B05B 7/2491; B05B 7/0081; B05B 7/22; G02B 1/14; A45D 44/22; F24F 6/025; G06F 3/041
(Continued)

(56) References Cited

U.S. PATENT DOCUMENTS

2004/0260016 A1* 12/2004 Louwet .................... C09D 5/24
524/817
2008/0029614 A1* 2/2008 Dore ....................... B05B 12/02
239/8
(Continued)

FOREIGN PATENT DOCUMENTS

JP 4016934 B2 12/2007
JP 5032389 B2 9/2012
(Continued)

OTHER PUBLICATIONS

Horii, T., Li, Y., Mori, Y. et al. "Correlation between the hierarchical structure and electrical conductivity of PEDOT/PSS", Jul. 1, 2014, Polymer Journal, vol. 47, pp. 695-699 (Year: 2015).*
(Continued)

*Primary Examiner* — Qingzhang Zhou
*Assistant Examiner* — Kevin Edward Schwartz
(74) *Attorney, Agent, or Firm* — Oblon, McClelland, Maier & Neustadt, L.L.P.

(57) ABSTRACT

A fine water discharge device includes a case having a flow path allowing a first space and a second space to communicate with each other, a blower which is disposed in the flow path, introduces air in the first space into the flow path, and discharges the air introduced into the flow path into the second space, a fine water generating unit which is disposed in the flow path and in which a plurality of the particles are laminated as a film-shaped conductive polymer film portion on an outer surface of a honeycomb member, and the
(Continued)

particles are transitioned between an adsorption state where water is adsorbed and a discharge state where the adsorbed water is discharged to the air, an electrifying portion electrically connected to the honeycomb member to perform electrification, and a controller which is a control portion controlling the blower and the electrifying portion.

11 Claims, 11 Drawing Sheets

(51) Int. Cl.

| | |
|---|---|
| ***B05B 7/00*** | (2006.01) |
| ***B05B 7/22*** | (2006.01) |
| ***F24F 6/02*** | (2006.01) |
| ***G02B 1/14*** | (2015.01) |
| *A45D 44/22* | (2006.01) |
| *G06F 3/041* | (2006.01) |

(52) U.S. Cl.
CPC ................ *F24F 6/025* (2013.01); *G02B 1/14* (2015.01); *A61M 11/003* (2014.02)

(58) Field of Classification Search
USPC .......................................................... 239/138
See application file for complete search history.

(56) References Cited

U.S. PATENT DOCUMENTS

| | | | | |
|---|---|---|---|---|
| 2011/0162528 | A1* | 7/2011 | Yamaguchi ............ | A61H 33/12 261/78.2 |
| 2011/0221079 | A1* | 9/2011 | Yamasaki ............... | A61L 9/145 261/135 |
| 2013/0140649 | A1* | 6/2013 | Rogers ................ | H01L 29/0669 438/48 |
| 2014/0327172 | A1* | 11/2014 | Yamauchi ............. | G03F 7/0002 264/148 |

FOREIGN PATENT DOCUMENTS

| | | | |
|---|---|---|---|
| JP | 5202720 | B2 * | 6/2013 |
| JP | 2016-176658 | A | 10/2016 |
| JP | 2017-60939 | A | 3/2017 |
| JP | 2017-116130 | A | 6/2017 |
| JP | 2018-54258 | A | 4/2018 |
| JP | 2019-18195 | A | 2/2019 |

OTHER PUBLICATIONS

Machine Translation of JP-5202720-B2 Description, Oct. 2023, Espacenet, pp. 1-22 (Year: 2023).*
Machine Translation of JP-2017060939—A Description, Oct. 2023, Espacenet, pp. 1-12 (Year: 2023).*
International Search Report issued on May 21, 2019 in PCT/JP2019/007674 filed on Feb. 27, 2019, 2 pages.

* cited by examiner

FINE WATER DISCHARGE DEVICE

TECHNICAL FIELD

The present invention relates to a fine water discharge device.

BACKGROUND ART

For example, in the related art, an electrostatic atomizer disclosed in PTL 1 below is known. The electrostatic atomizer of the related art includes a water transport unit which transports water by a capillary phenomenon, a heat exchange unit which supplies condensed water generated by cooling air on a heat absorbing surface to the water transport unit, an application electrode which applies a voltage to the water transported by the water transport unit, a counter electrode which is located to face the water transport unit, and a high voltage application unit which applies a high voltage between the application electrode and the counter electrode. Then, in the electrostatic atomizer of the related art, water retained at a distal end portion of the water transport unit is atomized toward the counter electrode by the high voltage applied by the high voltage application unit, and thus, nano-ion mist having a nano-sized and strong electric charge is generated.

Further, in the related art, for example, a negative ion and nano-mist generator disclosed in PTL 2 below is also known. The nano-mist generator of the related art includes a treatment chamber through which outside air passes by a feeder, a water storage section which is provided in a lower portion of the treatment chamber, a mortar-shaped rotation member of which a lower portion is submerged in the water storage section and a diameter increases upward, and a cylindrical porous body which is located on an outer periphery of the rotation member and rotates together with the rotation member and through which water and air scattered by a centrifugal force caused by the rotation can pass. Further, in the nano-mist generator of the related art, an air guide tube which is installed at an interval on an outer periphery of a counter body and guides the outside air flowing in from above the rotation member to an outer periphery of the porous body is provided, and a pair of large flow passage and small flow passage are formed between the air guide tube and the porous body. Accordingly, a pressure difference is generated in an air flow to generate a turbulence, and a large amount of negative ions and nano-mist are generated.

CITATION LIST

Patent Literature

PTL 1: Japanese Patent No. 4016934
PTL 2: Japanese Patent No. 5032389

SUMMARY OF INVENTION

Technical Problem

However, since the nano-mist generator of the related art generates nano-sized mist by crushing large water particles, particle sizes of the water particles become large and a particle size distribution of the water particles tends to widen. Further, since the nano-ion mist generated by the electrostatic atomizer of the related art has a strong electric charge and the nano-mist generated by the nano-mist generator of the related art is negatively charged, for example, the water particles may cause suction or repulsion against the human body. Accordingly, the generated water particles may not enter (cannot infiltrate) the inside of a surface of a horny layer of a human body.

Further, the electrostatic atomizer of the related art requires a Peltier element for condensing water in air and a high-voltage power supply for discharging, and there is a concern that the device becomes complicated and large in size. Further, the nano-mist generator of the related art requires a water tank, an air guide tube, a rotation member, or the like, and there is a concern that the device may become large in size.

The present invention is made to solve the above problems. That is, an object of the present invention is to provide a fine water discharge device capable of aligning a particle size distribution and discharging uncharged fine water.

Solution to Problem

In order to solve the above problem, according to an aspect of the present invention, there is provided a fine water discharge device including:

a case which has a flow path allowing a first space and a second space to communicate with each other; an air blowing unit which is disposed in the flow path, introduces air in the first space into the flow path, and discharges the air introduced into the flow path into the second space; a fine water generating unit which is disposed in the flow path, includes a base material portion and a plurality of particles having a core-shell structure including a core portion forming a nucleus and a shell portion formed of a polymer material having a polar functional group capable of hydrogen bonding to cover the core portion, and in which at least one of the base material portion and the particles has conductivity, the plurality of the particles are laminated in a film shape on an outer surface of the base material portion, and states of the particles are transitioned between an adsorption state where water is adsorbed and a discharge state where the adsorbed water is discharged to the air to generate fine water; an electrifying portion electrically connected to the base material portion of the fine water generating unit to electrify the base material portion; and a control portion which controls the air blowing unit and the electrifying portion, in which the control portion includes a discharge control portion which executes a discharge mode of introducing the air in the first space into the flow path by the air blowing unit, electrifying the base material portion of the fine water generating unit by the electrifying portion to discharge the water adsorbed on the particles of the fine water generating unit to the air introduced into the flow path as the uncharged fine water having a particle size of 50 nanometers or less through an opening of a channel formed by the plurality of laminated particles, and discharging the fine water to the second space together with the air introduced into the flow path by the air blowing unit, and a discharge preparation control portion which executes a discharge preparation mode of introducing the air in the first space or the second space into the flow path by the air blowing unit and non-electrifying the base material portion by the electrifying portion to adsorb the water introduced into the flow path to the particles through the channel from the opening.

According to this, the plurality of particles are laminated in a film shape on the outer surface of the base material portion formed in a honeycomb shape to form the fine water generating unit. When the plurality of particles are laminated, a nanometer-sized channel is formed between the particles, more specifically, between the shell portions of the particles. Since many polar functional groups are distributed in this channel, the water adsorbed by the particles in the adsorption state associated with the discharge preparation mode can be quickly moved toward the base material portion. Meanwhile, the adsorbed water quickly moves through the channel in the discharge state associated with the discharge mode and is discharged into the air. In this case, since the channel is formed by the plurality of laminated particles, a large number of openings for discharging the water corresponding to the channel can exist. Accordingly, a particle size distribution of the fine water discharged from the fine water discharge device can be aligned to be 50 nanometers or less.

Further, in the fine water discharge device, the discharge control portion executes the discharge mode so that the electrifying portion electrifies the base material portion. As a result, temperatures of the particles increase, and the fine water can be discharged. Therefore, the fine water discharge device can discharge a large amount of uncharged fine water into the second space without applying an electric charge to the fine water. Accordingly, the fine water discharged from the fine water discharge device is uncharged and has a small particle size of 50 nanometers or less, and thus, the fine water easily enters (infiltrates) a keratin of a human body, for example. As a result, the fine water can infiltrate the inside of the keratin and can contribute satisfactorily to moisturizing of a skin, for example.

Further, in the fine water discharge device, the discharge preparation control portion executes the discharge preparation mode so that the fine water generating unit (more specifically, particles) can adsorb water in air. Accordingly, in order to adsorb water and discharge fine water, for example, it is not necessary to provide a water tank, a high-voltage power supply, an air guide tube, or the like, and it is possible to reduce a size of the fine water discharge device.

DESCRIPTION OF EMBODIMENTS

Figure 1:
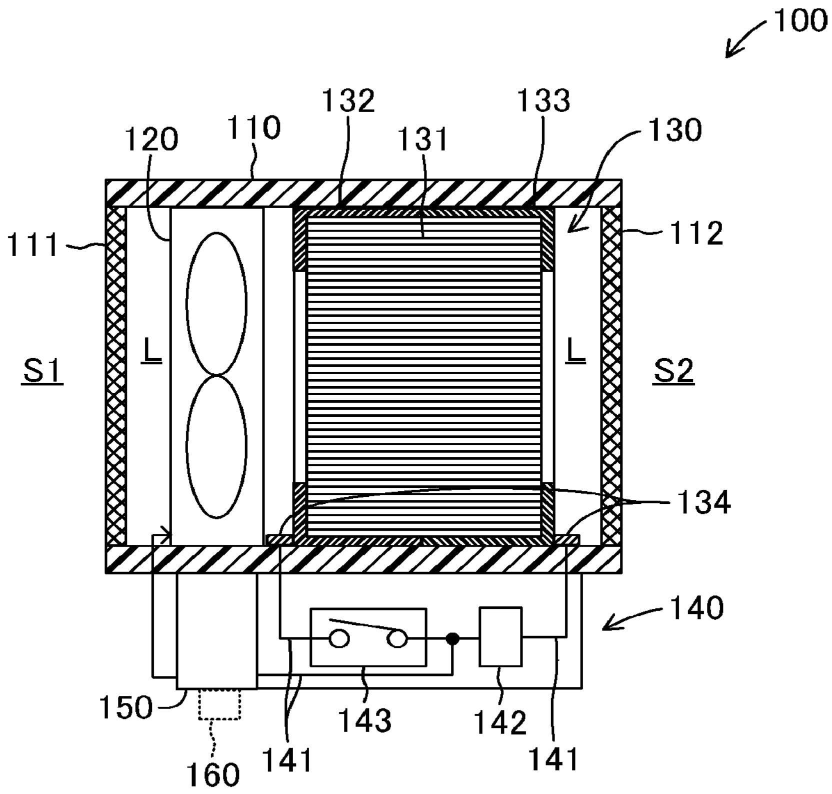
FIG. 1 is a cross-sectional view illustrating a configuration of a fine water discharge device according to an embodiment of the present invention.
Figure 2:
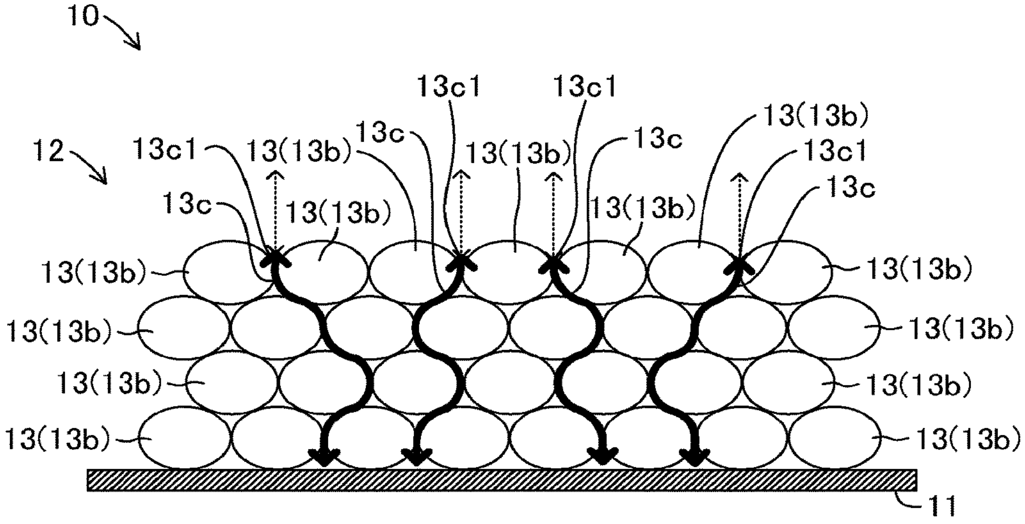
FIG. 2 is a partial cross-sectional view illustrating a fine water discharging element constituting the fine water generating unit of FIG. 1.

Hereinafter, embodiments of the fine water discharge device according to the present invention will be described. For example, a fine water discharge device 100 can be applied to beauty equipment (specifically, moisturizer, booster, vehicle mountable beauty equipment, or the like). As illustrated in FIG. 1, the fine water discharge device 100 includes a nano-sized water particle discharge element 10 (fine water generating unit 130 described later). The nano-sized water particle discharge element 10 is capable of transitioning between an adsorption state in which water contained in air is adsorbed and a discharge state in which the adsorbed water is discharged into air. As illustrated in FIG. 2, the nano-sized water particle discharge element 10 is formed in a sheet shape. The nano-sized water particle discharge element 10 includes a base material portion 11 and a conductive polymer film portion 12 (hereinafter, simply referred to as a "film portion 12") which is formed in a film shape on an outer surface of the base material portion 11.

For example, the base material portion 11 is a metal foil formed of stainless steel which is a stainless-steel based metal out of a metal material such as the stainless-steel based metal or a copper-based metal, a carbon material (carbon paper, graphite, or the like), a conductive ceramic material (for example, ITO, or the like), and a conductive resin material (for example, metal-deposited film, nano-silver coating, CNT coating, or the like), which are conductive materials, and has conductivity. As will be described later, the base material portion 11 generates heat when the base material portion 11 is electrified.

The film portion 12 is formed in a film shape by dispersing particles 13 having a core-shell structure in a solvent, applying (application step) a dispersion liquid in which the particles 13 are dispersed to the outer surface of the base material portion 11, and then drying (drying step) the applied dispersion liquid. That is, the fine water discharging element 10 is manufactured according to a manufacturing method including the application step of applying the dispersion liquid in which the particles 13 are dispersed to the conductive base material portion 11 and the drying step of drying the particles 13 applied to the base material portion 11 after the application step. As conceptually illustrated in FIG. 2, according to the manufacturing method, the plurality of particles 13 are formed in a layer shape (film shape) to have a certain degree of regularity (most densely) and to be laminated with a plurality of stages (four stages in FIG. 2). Here, regarding characteristics and components of the dispersion liquid, a solvent is water, a solid content concentration is 1 to 3(%), a viscosity is 10 to 200 (mPa·s), pH is 1 to 3, and antifungal agent is added as an additive. Moreover, a drying temperature in the drying step is 100° C. or less.

The particles 13 transition from the discharge state to the adsorption state when the base material portion 11 is not electrified (that is, a state where heat is not generated), and the particles 13 transition from the adsorption state to the discharge state when the base material portion 11 is electrified (that is, a state where heat is generated). Particle size of the particles 13 in the present embodiment is set to about 5 nanometers. Accordingly, the plurality of particles 13 are laminated with a certain degree of regularity on the outer surface of the base material portion 11 to form the film portion 12. Moreover, the "particle size" described in the present specification and claims is an average value of particle sizes of a plurality of randomly selected particles or a plurality of particles existing in a unit volume or a unit area.

Here, the film portion 12 is formed so that a thickness (film thickness) when the plurality of particles 13 are laminated on the outer surface of the base material portion 11 is 1 to 30 micrometers. The particles 13 in the present embodiment are formed of a conductive polymer, and specifically, PEDOT/PSS (poly (3,4-ethylenedioxythiophene)-poly (styrene sulfonic acid)), which is one of the thiophene-based conductive polymers. Therefore, the film portion 12 in the present embodiment is formed to include the particles 13 formed of PEDOT/PSS, and thus, is a thiophene-based conductive polymer.

Figure 3:
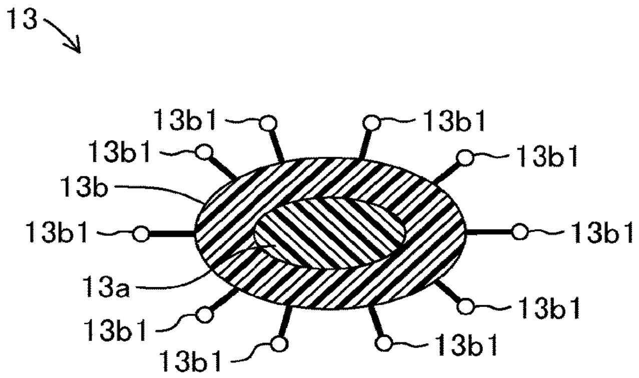
FIG. 3 is a cross-sectional view illustrating a composition of particles of FIG. 2.

As illustrated in FIG. 3, the particle 13 includes a core portion 13*a* and a shell portion 13*b*. The core portion 13*a* of the particle 13 forms a nucleus of the particle, and, for example, is formed of poly (3,4-ethylenedioxythiophene), that is, PEDOT, which is a polymer material out of the polymer material or an inorganic material. The shell portion 13*b* of the particle 13 is formed of a polymer material having a polar functional group 13*b*1 capable of hydrogen bonding and covers the core portion 13*a*.

Specifically, the shell portion 13*b* is formed of poly (styrene sulfonic acid), that is, PSS, which is polystyrene sulfonic acid out of polystyrene sulfonic acid, polyvinyl sulfonic acid, polyvinyl pyrrolidone, polyvinyl alcohol, and sodium polyacrylate. Here, the PSS forming the shell portion 13*b* includes a sulfonic acid group ($-SO_3H$) which is at least one of a sulfonic acid group ($-SO_3H$), a carboxyl group ($-COOH$), a hydroxyl group ($-OH$), an amino group ($-NH_2$), an amid group ($-C{=}ONH-$), and a pyrrolidone group ($NCOC_3H_6$), which are the polar functional groups 13*b*1 capable of hydrogen bonding.

Here, the PEDOT/PSS which is the particle 13 is set so that a weight ratio of ethylenedioxythiophene (EDOT) which is a monomer of PEDOT and PSS is 1:3 to 1:10, more preferably 1:4 to 1:6.

When the base material portion 11 is not electrified, an amount of water adsorbed by the film portion 12, that is, the particles 13 (shell portion 13*b*) increases with the elapse of time, and the fine water discharging element 10 is stabilized in a state of a saturated water absorption rate. Further, when the base material portion 11 is electrified and a temperature of the film portion 12, that is, the particles 13 increases to be equal to or more than a discharge temperature, the fine water discharging element 10 discharges the water bonded to the polar functional group 13*b*1 of the shell portion 13*b* of the particles 13 as uncharged (non-electrified) water particles (fine water described later). Here, as a film thickness of the film portion 12 provided in the base material portion 11 decreases, the number of particles 13 which are the conductive polymers supported by the base material portion 11 relatively decreases, and thus, the amount of water adsorbed decreases relatively. Meanwhile, as the film thickness of the film portion 12 provided in the base material portion 11 increases, the number of particles 13 which are the conductive polymers supported by the base material portion 11 relatively increases, and thus, the amount of water adsorbed increases relatively.

Then, in the fine water discharging element 10 configured to include the particles 13 having a core-shell structure, an adsorption speed of water in air in the adsorption state and a discharge speed of water into air in the discharge state are faster than in a general moisture absorbent such as silica gel. Further, in the fine water discharging element 10 configured to include the particles 13 having a core-shell structure, the particle size of the water particles of the water discharged in the discharge state is distributed within a very small particle size distribution range of 2 nanometers to 50 nanometers. Hereinafter, these things will be described in order.

First, the adsorption speed and the discharge speed of water will be described. In the fine water discharging element 10, the particles 13 formed of PEDOT/PSS are laminated on the base material portion 11. In this case, as illustrated in FIG. 2, the particles 13 are laminated in an aligned state in the film portion 12. Further, the PSS constituting the shell portion 13*b* of the particles 13 has many sulfonic acid groups ($-SO_3H$) which are the polar functional groups 13*b*1 capable of hydrogen bonding, and as illustrated in FIG. 3, has sulfonic acid groups ($-SO_3H$) which are the many polar functional groups 13*b*1 around the shell portion 13*b*. Therefore, water contained in the air is bonded to the sulfonic acid group ($-SO_3H$) which is in contact with the air by hydrogen bond, for example, as bound water having a particle size of 2 nanometers or less.

In this case, when the amount of water on the surface of the film portion 12 is large and the amount of water inside the film portion 12 is small, the shell portion 13*b* of the particles 13 attempts to move the adsorbed water from the surface of the film portion 12 toward an inside of the film portion 12 by using a difference in water concentration as a driving source. Meanwhile, as illustrated by thick arrows in FIG. 2, inside the film portion 12, a channel 13*c* (hereinafter, this channel 13*c* is referred to as a "nanochannel 13*c*") having a nanometer-sized flow path diameter (for example, about 2 nanometers) is formed between the shell portion 13*b* and the shell portion 13*b* of the plurality of laminated particles 13. As illustrated in FIG. 2, the nanochannels 13*c* are connected to each other inside the film portion 12. Moreover, the flow path diameter of the nanochannel 13*c* represents a value obtained by averaging the flow path diameters of a plurality of randomly selected nanochannels 13*c*, or a plurality of nanochannels 13*c* existing in a unit volume or a unit area or the like.

Many sulfonic acid groups (—$SO_3H$), which are polar functional groups 13*b*1, are distributed in the nanochannel 13*c*, and water molecules (water) existing on the surface of the film portion 12 move at a high speed to the inside of the film portion 12 through the sulfonic acid groups (—$SO_3H$) existing in the nanochannel 13*c*. As a result, the water in the air existing on the surface of the film portion 12 moves at a high speed to the inside of the film portion 12 due to the difference in water concentration, and a large amount of water can be adsorbed and retained from the air at a high speed. Here, the water retained inside the film portion 12 is bound water or bounded water, and free water can hardly exist.

Further, since the water moves by using the difference in water concentration as a driving source in this way, when the amount of water inside the film portion 12 is large and the amount of water on the surface of the film portion 12 is small, that is, when air is dried, contrary to the above-mentioned adsorption, the sulfonic acid group (—$SO_3H$), which is a polar functional group 13*b*1 existing in the nanochannel 13*c*, is transmitted, and thus, the retained (adsorbed) water moves at a high speed from the inside of the film portion 12 toward the surface of the film portion 12. As a result, the water retained (adsorbed) inside the film portion 12 moves at a high speed to the surface of the film portion 12 due to the difference in water concentration, and the film portion 12 (particles 13) can discharge a large amount of water into the air at a high speed as the water particles as the bound water. Further, even when humidity of outside air is high, a temperature of the film portion 12 increases by electrifying the base material portion 11, the film portion 12 (particles 13) can discharge a large amount of water into the air at a high speed as the water particles as the bound water.

Figure 4:
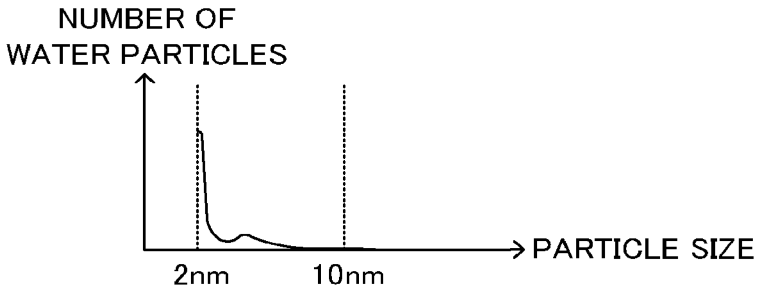
FIG. 4 is a diagram illustrating a measurement result of particle sizes of water particles discharged from the fine water discharging element of FIG. 2.
Figure 5:
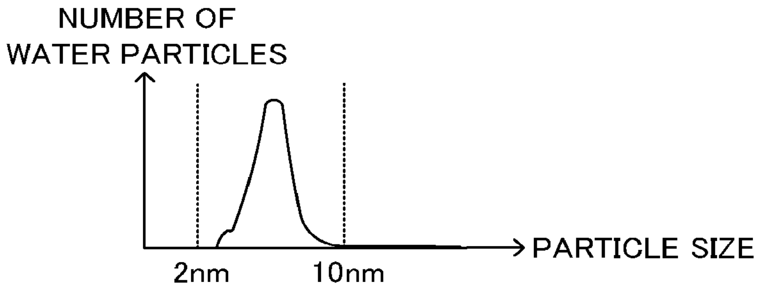
FIG. 5 is a diagram illustrating a measurement result of the particle size of the water particles after the water particles are discharged from the fine water discharging element of FIG. 2 and a predetermined time has elapsed.
Figure 6:
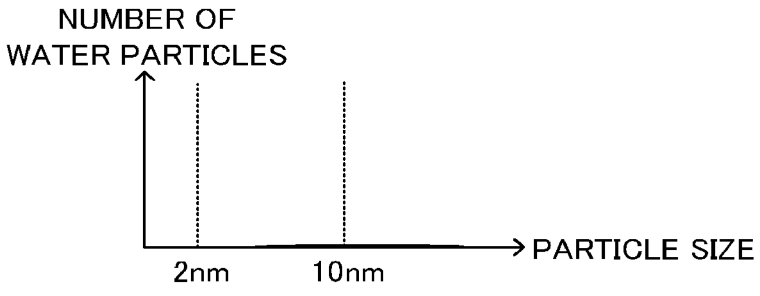
FIG. 6 is a diagram illustrating a measurement result of the particle size of the water particles in indoor air where the water particles are discharged from the fine water discharging element of FIG. 2.

Next, it will be described that the water particle size of the water discharged from the film portion 12 (particles 13) is small in the discharge state. In the following, particularly, water having a small water particle size, specifically, water (water cluster) having a particle size of 50 nanometers or less is referred to as "fine water". As illustrated in FIG. 4, a water particle size distribution immediately after being discharged from the fine water discharging element 10 configured to include the particles 13 formed of PEDOT/PSS illustrates the maximum value at 2 nanometers which is a lower limit of a measurement range and is up to around 10 nanometers. Further, as illustrated in FIG. 5, after a predetermined time (for example, 40 seconds) has elapsed from the discharge of water, the water particles (fine water) aggregate (cluster) and the water particle size distribution tends to move to a large particle size side (50 nanometers or less). A peak value of the water particle size distribution is 10 nanometers or less as illustrated in FIGS. 4 and 5. Here, in this measurement, as illustrated in FIG. 6, nanometer-sized water particles are hardly measured in indoor air. Moreover, in the measurement of the water particle size distribution, the measurement is performed using a scanning mobility particle sizer (SMPS) of measuring the particle distribution in a submicron region by classifying the water particles (fine water) using electrical mobility and measuring a number concentration per unit volume (1 cc) using a condensed particle counter.

It is considered that the reason why the fine water discharging element 10 discharges the water having a small water particle size, that is, discharges the fine water, is as follows. As described above, the particles 13 having the core-shell structure in the present embodiment are PEDOT/PSS, and PEDOT is present in the core portion 13*a* and PSS exists in the shell portion 13*b*. PSS has a sulfonic acid group (—$SO_3H$) which is a hydrophilic group as the polar functional group 13*b*1, and is distributed in large numbers on the outer surface and the inside of the shell portion 13*b*.

Therefore, as described above, a large amount of bound water bonded to the sulfonic acid group (—$SO_3H$) exists inside the nanochannel 13*c*. Here, it is considered that the reason why the bound water is unevenly distributed in the nanochannels 13*c* on the outer surface of the shell portion 13*b* and the bound water does not enter the inside of the shell portion 13*b* is that PEDOT of the core portion 13*a* pushes the bound water to the outer surface of the shell portion 13*b* due to hydrophobicity of PEDOT.

Moreover, the reason why the bound water having a size of several nanometers (specifically, the particle size is 2 nanometers) is discharged when the fine water is generated is that, when the base material portion 11 is electrified, the temperature of the film portion 12 (particles 13) increases and thermal energy is supplied to the bound water (more specifically, water molecules). As a result, in the fine water discharging element 10, motility of the bound water increases. As a result, the bound water aggregates (clusters) at a spout 13*c*1 (specifically, a pore having diameter of about 2 nanometers), which is an opening in which a large number of bound water existing in the nanochannel 13*c* exists on the surface of the film portion 12 corresponding to the flow path diameter of the nanochannel 13*c*, and is discharged into the air as the fine water which is uncharged (non-electrified) and is 50 nanometers or less. In addition, the bound water keeps a shape of the bound water and is discharged as the fine water.

Further, the nano-sized water particle discharge element 10 is rich in viscoelasticity due to a network between the particles 13 formed to have a core-shell structure from PEDOT/PSS, and stably exists even at high temperature and high humidity. As a result, the nano-sized water particle discharge element 10 has performance which can be applied to an actual usage environment as described later.

Figure 7:
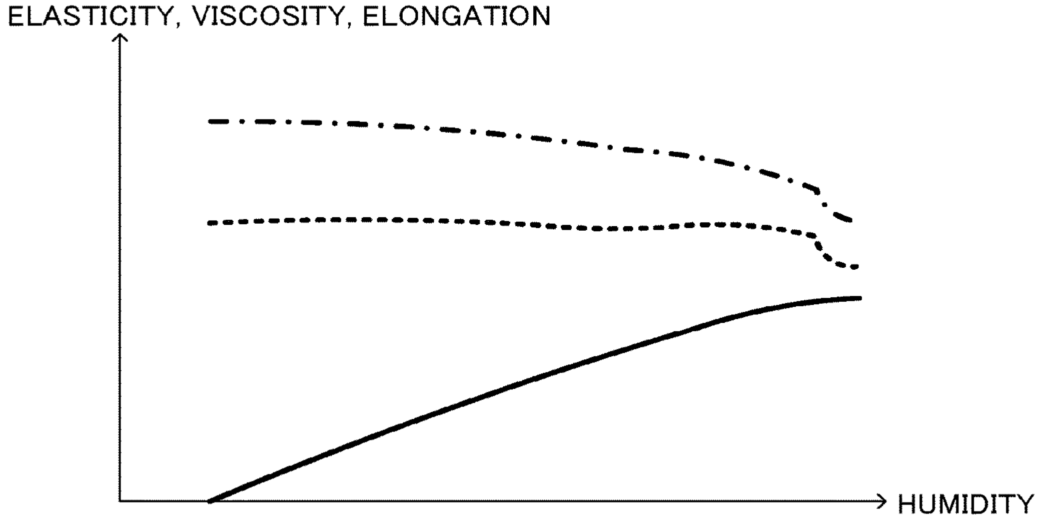
FIG. 7 is a graph illustrating the humidity dependence of dynamic viscoelastic property of the fine water discharging element of FIG. 2.
Figure 8:
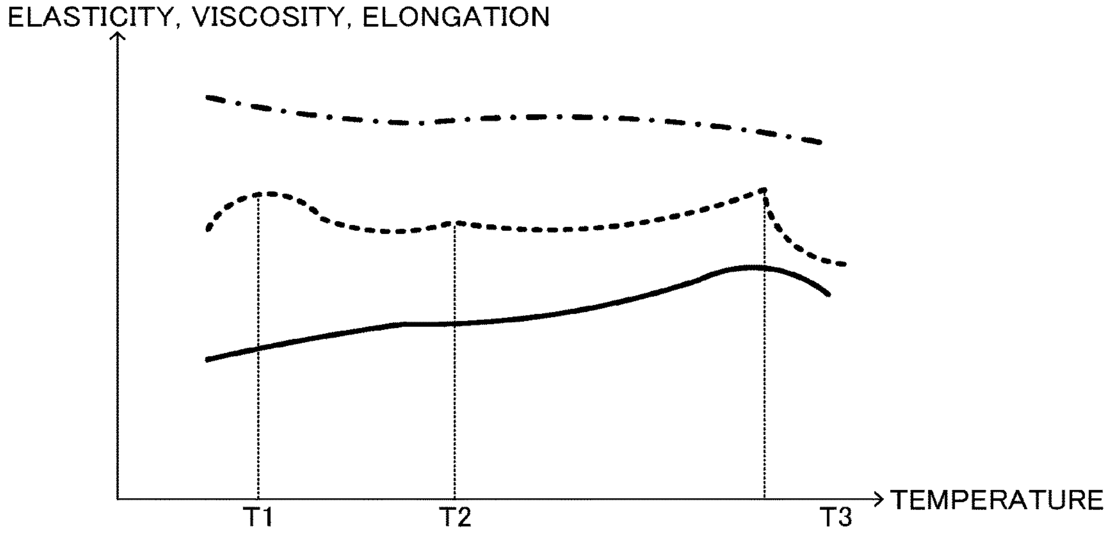
FIG. 8 is a graph illustrating a temperature dependence of the dynamic viscoelastic property of the fine water discharging element of FIG. 2.

Specifically, in the dynamic viscoelastic property of the film portion 12 including the particles 13, regarding humidity dependence, as illustrated in FIG. 7, as described above, adsorption (moisture absorption) progresses as humidity increases, elongation indicated by a solid line increases, but viscosity indicated by a broken line and elasticity indicated by a dashed line are appropriately maintained. In the dynamic viscoelastic property of the film portion 12 including the particles 13, regarding temperature dependence, as illustrated in FIG. 8, the viscosity indicated by a broken line is appropriately maintained although peaks occur at a temperature T1, a temperature T2, and a temperature T3 depending on the particles 13 having the core-shell structure, and the elasticity indicated by a dashed line is also appropriately maintained.

Moreover, the temperature T1 is a β relaxation temperature (for example, −60° C.) of the sulfonic acid group (—$SO_3H$) constituting the particles 13. Further, the temperature T2 is a glass transition temperature (for example, 60° C.) of the shell portion 13*b* (PSS) constituting the particles 13. Further, the temperature T3 is a melting point (for example, 260° C.) of the core portion 13*a* (PEDOT) constituting the particles 13.

Returning to FIG. 1, the fine water discharge device 100 includes a case 110, a blower 120 which is an air blowing unit, the fine water generating unit 130, an electrifying portion 140, and a controller 150 which is a control portion.

The case 110 is formed in a tubular shape in which both ends are open and extend in a front-rear direction so as to have a flow path L through which air flows inside the case 110. The flow path L is open toward a first space S1 which is a space in front of the case 110 and is open toward a second space S2 which is a space behind the case 110. A filter 111 and a filter 112 having air permeability are mounted on the opening of a first space S1 side and the opening of a second space S2 side, respectively. For example, the first space S1 and the second space S2 are spaces in the same room, and a user receives a supply of the fine water on the second space S2 side.

The first space S1 and the second space S2 communicate with each other through the flow path L. Inside the flow path L, the blower 120 and the fine water generating unit 130 (nano-sized water particle discharge element 10) are disposed in this order from the first space S1 side toward the second space S2 side of the case 110.

The blower 120 which is the air blowing unit is rotationally driven in a first direction to introduce air in the first space S1 into the flow path L, and discharges the air introduced into the flow path L to the second space S2. Further, the blower 120 rotationally driven in a second direction opposite to the first direction to introduce the air in the second space S2 into the flow path L, and discharges the air introduced into the flow path L to the first space S1. For example, the blower 120 is a shaft blower. The blower 120 is electrically connected to the controller 150 and is driven according to a control command value transmitted from the controller 150. Moreover, since the blower 120 is PWM controlled, the control command value is calculated by a duty ratio.

The fine water generating unit 130 generates and discharges fine water into the air introduced into the flow path L by the blower 120, and adsorbs the water of the air. The fine water generating unit 130 is configured to include the above-mentioned fine water discharging element 10. Accordingly, in the fine water generating unit 130, when the base material portion 11 of the fine water discharging element 10 is not electrified, the state of the particles 13 having the core-shell structure constituting the film portion 12 is transitioned, and the particles 13 adsorb (adsorption state) the water of the air introduced into the flow path L. Further, in the fine water generating unit 130, when the base material portion 11 of the fine water discharging element 10 is electrified, the state of the particles 13 is transitioned, and the water adsorbed by the particles 13 is discharged as the fine water to the air introduced into the flow path L (discharge state).

Figure 9:
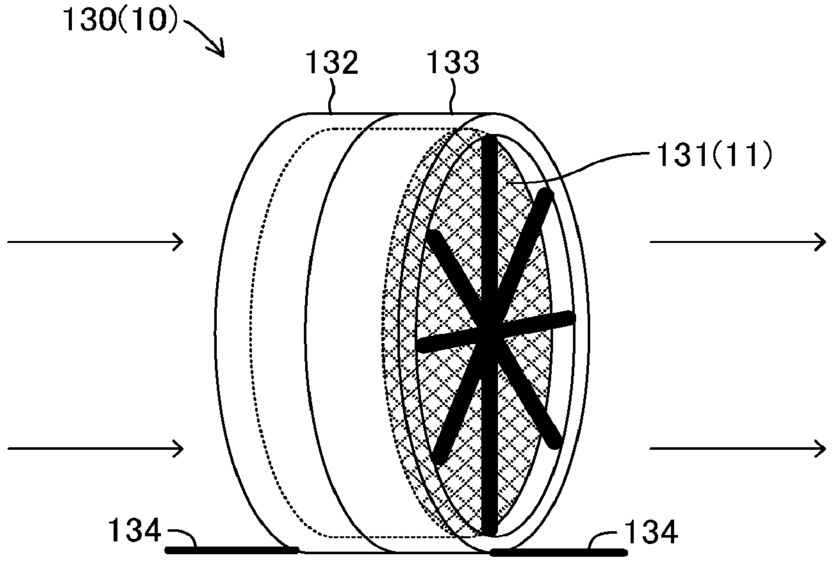
FIG. 9 is a perspective view illustrating a configuration of the fine water generating unit of FIG. 1.
Figure 10:
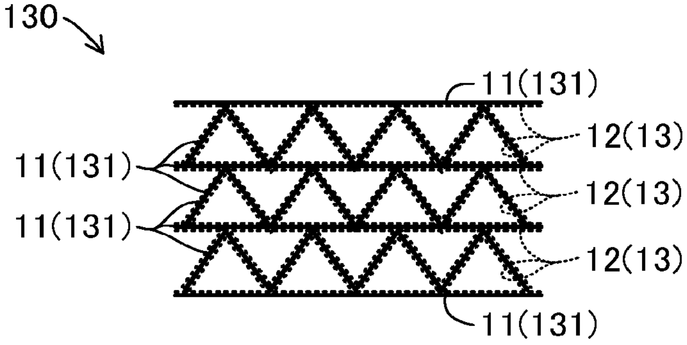
FIG. 10 is a cross-sectional view illustrating configurations of a base material portion and a film portion (particles) constituting the fine water generating unit of FIG. 9.

As illustrated in FIG. 9, the fine water generating unit 130 includes a columnar honeycomb member 131 having conductivity. The honeycomb member 131 constitutes the base material portion 11 of the fine water discharging element 10, and is formed of a conductive material, for example, 20 chromium 5 aluminum-based ferritic stainless steel. As illustrated in FIG. 10, the honeycomb member 131 (that is, the base material portion 11) is formed in a honeycomb shape including a corrugated plate and a flat plate. In the honeycomb member 131 (base material portion 11), the corrugated plate and the flat plate are insulation-processed. As illustrated in FIG. 10, the particles 13 having a core-shell structure are applied to the outer surface of the honeycomb-shaped base material portion 11 (that is, the honeycomb member 131) to form the film portion 12.

Further, as illustrated in FIGS. 1 and 9, the fine water generating unit 130 includes an annular first case member 132 and an annular second case member 133 which surround an outer peripheral portion of the honeycomb member 131 (base material portion 11). For example, the first case member 132 is disposed on the first space S1 side of the case 110, and is reinforced by a flange provided so as to abut on the first space S1 side of the honeycomb member 131 (base material portion 11). For example, the second case member 133 is disposed on the second space S2 side of the case 110 and is reinforced by a flange provided so as to abut on the second space S2 side of the honeycomb member 131 (base material portion 11).

Further, in the fine water generating unit 130, an electrode 134 is formed to protrude outward from the honeycomb member 131, that is, the base material portion 11 formed in a honeycomb shape, as illustrated in FIGS. 1 and 9. More specifically, one end of the electrode 134 is electrically connected to the honeycomb member 131 (base material portion 11), and the other end thereof protrudes outward from openings of the first case member 132 and the second case member 133. The electrifying portion 140 is electrically connected to the other end of the electrode 134.

The fine water generating unit 130 including the honeycomb member 131, the first case member 132, the second case member 133, and the electrode 134 is formed as a cartridge that can be detachably assembled to the flow path L of the case 110. In a state where the fine water generating unit 130 to be attached and detached as a cartridge is assembled to the flow path L, the air introduced into the flow path L flows through the fine water generating unit 130 in a direction of an arrow as illustrated by the arrow in FIG. 7.

As illustrated in FIG. 1, the electrifying portion 140 is electrically connected to the electrode 134 of the fine water generating unit 130, and electrifies the fine water generating unit 130 (more specifically, the honeycomb member 131, and the base material portion 11 of the fine water discharging element 10). As illustrated in FIG. 1, the electrifying portion 140 includes electric wires 141, a power supply 142, and a switch 143.

The electric wire 141 is an electric wire which electrically connects the power supply 142, the blower 120, and the electrode 134 of the fine water generating unit 130 to each other. For example, the power supply 142 is a commercial power supply, and can adopt a USB (Universal Serial Bus) power supply system. The switch 143 is arranged on the electric wire 141, and is, for example, a normally open type switch which opens a circuit when is not operated.

The switch 143 closes a circuit according to the control command value transmitted from the controller 150 to electrically connect the power supply 142, the blower 120, and the fine water generating unit 130 to each other, and opens the circuit to cut off the electrical connection between the power supply 142, the blower 120, and the fine water generating unit 130. As a result, the blower 120 is switched between an electrified state in which the blower 120 is rotationally driven in the first or second direction and a non-electrified state in which the rotational driving is stopped. Further, the fine water generating unit 130 is switched between an electrified state in which the honeycomb member 131 (base material portion 11) is electrified to generate the fine water and a non-electrified state in which the honeycomb member 131 (base material portion 11) is not electrified and does not generate the fine water.

Figure 11:
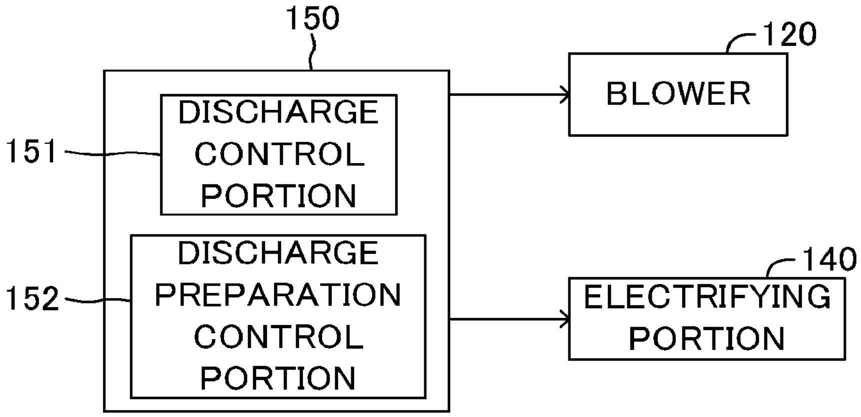
FIG. 11 is a block diagram of a controller of FIG. 1.

As illustrated in FIG. 11, the controller 150 which is the control portion includes a discharge control portion 151 and a discharge preparation control portion 152. The discharge control portion 151 executes a discharge mode which is an operation mode of the fine water discharge device 100, and controls the discharge of the fine water to the second space S2. The discharge preparation control portion 152 executes the discharge preparation mode which is the operation mode of the fine water discharge device 100, and controls a discharge preparation of the fine water to the second space S2.

The discharge mode executed by the discharge control portion 151 is an operation mode of causing the fine water generating unit 130 (nano-sized water particle discharge element 10) to generate the fine water. In addition, the discharge mode executed by the discharge control portion 151 is an operation mode of discharging the air, which is introduced into the flow path L from the first space S1 and includes the fine water, to the second space S2. Specifically, the discharge control portion 151 rotationally drives the blower 120 in the first direction by executing the discharge mode, introduces the air in the first space S1 into the flow path L, and discharges the air in the second space S2.

Then, the discharge control portion 151 closes the switch 143 of the electrifying portion 140 so as to electrify the fine water generating unit 130 (nano-sized water particle discharge element 10). As a result, the honeycomb member 131 (base material portion 11) of the fine water generating unit 130 (nano-sized water particle discharge element 10) is electrified. Accordingly, the temperature of the film portion 12 (particles 13) formed on the honeycomb member 131 (base material portion 11) increases to generate the fine water, and the fine water is discharged to the second space S2 together with the air introduced into the flow path L.

Meanwhile, the temperatures of the electrified honeycomb member 131 (base material portion 11) and film portion 12 (particles 13) increase by a range of 20° C. to 50° C. as compared with those of the non-electrified honeycomb member 131 and film portion 12. As a result, the bound water having a particle size of about 2 nanometers adsorbed to the particles 13 passes through the nanochannel 13*c* and condenses (clusters) and is discharged into the flow path L as the fine water having a particle size of 50 nanometers or less (discharge state), and the air introduced into the flow path L from the first space S1 is discharged from the second space S2 in a state of including the fine water. Moreover, in the discharge mode, first, the discharge control portion 151 electrifies only the honeycomb member 131 (base material portion 11) to increases the temperature of the film portion 12 (particles 13), and then can rotationally drive the blower 120 in the first direction while continuously executing the electrification on the honeycomb member 131 (base material portion 11).

Here, for example, regarding an amount of rotational drive of the blower 120, an amount of electricity applied to the fine water generating unit 130 (fine water discharging element 10), a surface area of the film portion 12 supported by the honeycomb member 131 (base material portion 11), or the like is set as follows. For example, assuming that a temperature of air in the first space S1 is 25° C. and a relative humidity of the air in the first space S1 is 40%, the fine water is included in the air introduced from the first space S1 into the flow path L, and the relative humidity of the air discharged from the second space S2 is set to be about 90%.

The discharge preparation mode executed by the discharge preparation control portion 152 is a mode (operation mode) of causing the fine water generating unit 130 (nano-sized water particle discharge element 10) to stop the generation of the fine water. In addition, the discharge preparation mode executed by the discharge preparation control portion 152 is a mode (operation mode) of discharging air from the first space S1 toward the second space S2 or from the second space S2 toward the first space S1 via the flow path L.

Specifically, the discharge preparation control portion 152 opens the switch 143 of the electrifying portion 140 so as to switch the fine water generating unit 130 (nano-sized water particle discharge element 10) to the non-electrified state. Accordingly, the honeycomb member 131 (base material portion 11) of the fine water generating unit 130 (nano-sized water particle discharge element 10) does not generate heat because the fine water generating unit 130 is in the non-electrified state, and as a result, the temperature of the film portion 12 (particles 13) formed on the honeycomb member 131 (base material portion 11) decreases.

Further, the discharge preparation control portion 152 rotationally drives the blower 120 in the first direction to discharge the air in the first space S1 into the second space S2. Alternatively, the discharge preparation control portion 152 rotationally drives the blower 120 in the second direction to discharge the air in the second space S2 into the first space S1. Accordingly, when the fine water generating unit 130 (nano-sized water particle discharge element 10) is in the non-electrified state, the film portion 12 (particles 13) formed in the honeycomb member 131 (base material portion 11) is cooled by the air flowing through the inside of the flow path L.

Meanwhile, in a state where the film portion 12 (particle 13) is cooled, as described above, the water of the air introduced into the flow path L is adsorbed by the sulfonic acid group (—$SO_3H$) which is the polar functional group 13*b*1 unevenly distributed in the nanochannel 13*c* (adsorption state). In this case, in the non-electrified state, thermal energy is not applied to the water (bound water) bonded to the sulfonic acid group (–$SO_3H$) which is the polar functional group 13*b*1, and as a result, the water (bound water) does not fly out of the nanochannel 13*c* as the fine water, and the water is stably adsorbed.

The fine water discharge device 100 of the present embodiment starts the operation when the user activates the controller 150, that is, turns on power. Specifically, when the controller 150 is activated, first, as a first step, the discharge preparation control portion 152 executes the discharge preparation mode, rotationally drives the blower 120 in the second direction, and introduces air from the fine water generating unit 130 toward the blower 120 inside the flow path L. In this case, the discharge preparation control portion 152 operates the blower 120 so that an operating time is t1 (s) and a wind speed is f1 (m/s).

In this way, in the first step, when the discharge preparation control portion 152 executes the discharge preparation mode, the water contained in the air flowing inside the flow path L from the second space S2 to the first space S1 is adsorbed (moisture-absorbed) by the film portion 12 (particles 13) supported by the honeycomb member 131 (base material portion 11). Then, when the discharge preparation control portion 152 operates the blower 120 at the wind speed f1 (m/s) for the operating time t1 (s), the blower 120 is stopped.

Subsequently, as a second step, the discharge control portion 151 executes the discharge mode. In the present embodiment, the discharge control portion 151 closes the switch 143 of the electrifying portion 140 and electrifies the honeycomb member 131 (base material portion 11) of the fine water generating unit 130. In this case, the discharge control portion 151 electrifies the honeycomb member 131 (base material portion 11) so that an electrification time is t2 (s) and electric power is P (w) in order to increases the temperature of the honeycomb member 131 (base material portion 11) by the range of 20° C. to 50° C. as compared with that of the non-electrified honeycomb member 131. Moreover, the operating time t2 (s) and the electric power P (w) can be arbitrarily set by the user.

Further, as a third step, the discharge control portion 151 electrifies the honeycomb member 131 (base material portion 11) and at the same time rotationally drives the blower 120 in the first direction to introduce the air from the blower 120 toward the fine water generating unit 130 inside the flow path L. In this case, the discharge control portion 151 operates the blower 120 so that the operating time is t2 (s) and the wind speed is f2 (m/s). For example, the wind speed f2 (m/s) can be arbitrarily set by the user according to a discharge distance of the fine water.

As described above, in the second step and the third step, the discharge control portion 151 executes the discharge mode. Accordingly, the temperature of the film portion 12 (particles 13) supported by the honeycomb member 131 (base material portion 11) increases by about 30° C. to discharge fine water, and the discharged fine water is discharged to the second space S2 together with the air flowing inside the flow path L. Then, when the discharge control portion 151 electrifies the honeycomb member 131 (base material portion 11) with the electric power P (w) for the electrification time t2 (s) and operates the blower 120 with the wind speed f2 (m/s) for the operating time t2 (s), the electrification to the honeycomb member 131 (base material portion 11) is cut off and the blower 120 is stopped.

Next, as a fourth step, the discharge preparation control portion 152 executes the discharge preparation mode, rotationally drives the blower 120 in the second direction, and introduces the air from the fine water generating unit 130 toward the blower 120 inside the flow path L. In this case, the discharge preparation control portion 152 operates the blower 120 so that the operating time is t3 (s) and the wind speed is f3 (m/s). Here, the wind speed f3 (m/s) in the fourth step is set to a value larger than the wind speed f1 (m/s) in the first step.

As described above, in the fourth step, the discharge preparation control portion 152 executes the discharge preparation mode. Accordingly, the honeycomb member 131 (base material portion 11) and the film portion 12 (particles 13) of which the temperatures have been increased by the electrification in the second step are cooled. Here, the wind speed f3 (m/s) in the fourth step is larger than the wind speed f1 (m/s) in the first step. Therefore, the air flows quickly inside the flow path L, and as a result, the honeycomb member 131 (base material portion 11) is quickly cooled. Meanwhile, the wind speed f1 (m/s) in the first step is smaller than the wind speed f3 (m/s) in the fourth step. Therefore, the air flows slowly inside the flow path L, and as a result, a contact time between the film portion 12 (particles 13) supported by the honeycomb member 131 (base material portion 11) and the air becomes relatively long, and thus, the water contained in the air is more reliably adsorbed (moisture-absorbed).

Then, the fine water discharge device 100 sets the above-mentioned first to fourth steps as one cycle, and repeats this cycle about 2 to 10 cycles, for example. Moreover, the number of cycles to be repeated is arbitrarily set by the user.

Figure 12:
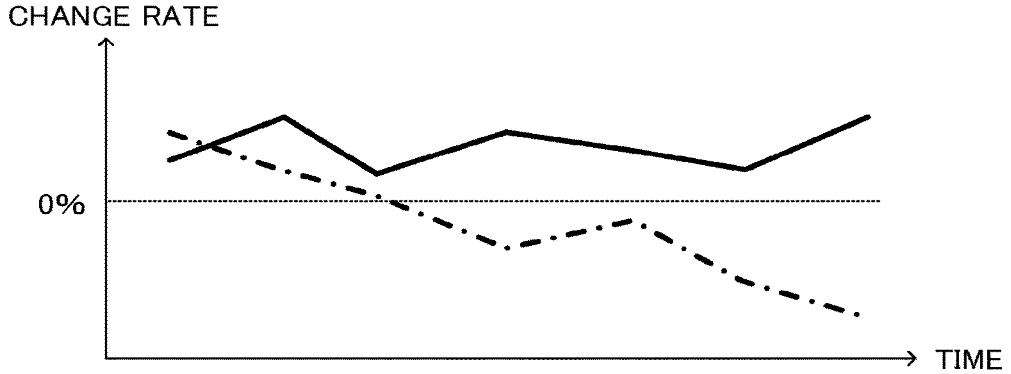
FIG. 12 is a diagram illustrating a measurement result of a time change rate of a water content of a keratin in a case where the fine water is discharged by the fine water discharge device of FIG. 1 and a case where water particles are discharged by a device of the related art.

Meanwhile, the above-mentioned fine water discharge device 100 can discharge the generated fine water in a state of the bound water similar to water (natural moisturizing factor) retained in a keratin of a human body and in an uncharged (non-electrified) state. Therefore, by exposing a skin of the user to the fine water discharged from the fine water discharge device 100, the user can obtain a moisturizing effect of the skin for a long time. This will be explained based on FIG. 12 which illustrates a comparison result of a time change rate of a water content of a keratin of a cheek in a case where the fine water is discharged by the fine water discharge device 100 and a case where nano-mist is discharged by the device of the related art.

Moreover, regarding the fine water discharged by the fine water discharge device 100 (nano-sized water particle discharge element 10), pH of the discharged fine water is 6.8 to 7.0, and even when the fine water comes into direct contact with a skin, it is safe because there are no reports of erythema or skin abnormalities. Further, a gas generated when the fine water discharge device 100 (nano-sized water particle discharge element 10) discharges the fine water includes only a trace amount of sulfur oxides below the environmental standard and does not affect the environment.

Generally, it is said that a keratinous gap of a human skin is about 50 nanometers. As described above, the fine water discharge device 100, that is, the nano-sized water particle discharge element 10, discharges the fine water of 50 nanometers or less in the uncharged (non-electrified) state and the state of the bound water. As a result, as illustrated by a solid line in FIG. 12, the fine water discharged from the fine water discharge device 100 (nano-sized water particle discharge element 10) efficiently infiltrates the inside of the keratin (inside of the skin) in the state of the bound water, and as a result, a water content of the keratin is unlikely to decrease with a passage of time. Therefore, the fine water can provide a moisturizing effect on the skin for a long time, for example, improvement of dry fine wrinkles, smoothing of a skin texture, improvement of sagging and firmness, suppression of excessive sebum secretion, moisturizing of an atopic skin (dry skin) can be expected.

Meanwhile, the device of the related art discharges nano-sized nano-mist in a charged and free water state. As a result, as illustrated by a dashed line in FIG. 12, the nano-mist discharged from the device of the related art infiltrate the inside of the keratin (inside of the skin) immediately after reaching the skin. However, the nano-mist infiltrates in the free water state, the nano-mist easily evaporates, and as a result, the water content of the keratin decreases with the passage of time. Therefore, it is difficult for the nano-mists to provide a moisturizing effect on the skin for a long time in the related art.

Moreover, as described above, the fine water is discharged as the temperature of the film portion 12 (particles 13) in which the fine water is supported by the honeycomb member 131 (base material portion 11) increases. Generally, it is said that the keratin has a high transdermal absorption rate at 32° C. to 39° C. Therefore, it can be considered that the discharge of the fine water at a warm temperature also facilitates the infiltration to the inside of the keratin (inside of the skin).

Further, depending on the user, a cream or the like (for example, APM (magnesium phosphate ascorpate) or the like) which infiltrates a beauty component such as vitamin C into the keratin (into the skin) may be applied to a cheek or the like. Meanwhile, the fine water discharged by the fine water discharge device 100 (nano-sized water particle discharge element 10) is uncharged (non-electrified), and can stably maintain a fine particle shape, that is, 50 nanometers or less even after the fine water is discharged. Therefore, for example, the fine water which has not infiltrated the inside of the keratin (inside of the skin) can be infiltrated together with the beauty component into epidermis of the skin, and as a result, a beauty component infiltration effect of infiltrating the beauty component into the keratin (into the skin) can be enhanced, and for example, skin whitening and skin firmness can be expected.

Meanwhile, the nano-mist discharged by the device of the related art is charged, and it is difficult to maintain a fine particle shape after the discharge. Therefore, for example, the nano-mist which has not infiltrated the inside of the keratin (inside of the skin) cannot infiltrate together with the beauty component into the epidermis of the skin when the particle size is larger than 50 nanometers, and as a result, the beauty component infiltration effect cannot be enhanced.

Here, when the fine water discharged from the fine water discharge device 100 to the second space S2 is supplied to the skin of the user, for example, a discharge-side opening (that is, nozzle) of the flow path L communicating with the second space S2 is formed in a blowout shape which exerts the Coanda effect and the fine water discharged from the case 110 can be directly supplied (touched) to the skin of the user. Further, for example, it is possible to supply the fine water to the skin and infiltrate the fine water through a face mask which covers a face of the user. Further, the second space S2 is partitioned by a tent, a capsule, or the like, the fine water is discharged from the case 110 into the tent, the capsule, or the like, and the fine water is supplied to the skin of the user who has entered the tent, the capsule, or the like and the fine water can be infiltrated. Furthermore, it is possible to supply the fine water to the skin (scalp) and can infiltrate the fine water through a hat (cap) or helmet worn by the user.

As can be understood from the above description, the fine water discharge device 100 according to the above embodiment includes the case 110 which has the flow path L allowing the first space S1 and the second space S2 to communicate with each other, the blower 120 which is the air blowing unit which is arranged in the flow path L, introduces air in the first space S1 into the flow path L, and discharges the air introduced into the flow path L into the second space S2, the fine water generating unit 130 which is disposed in the flow path L, includes the honeycomb member 131 (base material portion 11) formed in a honeycomb shape as the base material portion and the plurality of particles 13 having the core-shell structure including the core portion 13*a* forming a nucleus and the shell portion 13*b* formed of a polymer material having the polar functional group capable of hydrogen bonding to cover the core portion 13*a*, and in which at least one of the honeycomb member 131 (base material portion 11) and the particles 13 has conductivity, the plurality of the particles 13 are laminated as the film-shape conductive polymer film portion 12 on the outer surface of the honeycomb member 131 (base material portion 11), and states of the particles 13 are transitioned between the adsorption state where water is adsorbed and the discharge state where the adsorbed water is discharged to the air to generate fine water, the electrifying portion 140 electrically connected to the honeycomb member 131 (base material portion 11) of the fine water generating unit 130 to electrify the honeycomb member 131 (base material portion 11), and the controller 150 which is the control portion controlling the blower 120 and the electrifying portion 140, in which the controller 150 includes the discharge control portion 151 which executes the discharge mode of introducing the air in the first space S1 into the flow path L by the blower 120, electrifying the honeycomb member 131 (base material portion 11) of the fine water generating unit 130 by the electrifying portion 140 to discharge the water adsorbed on the particles 13 of the fine water generating unit 130 to the air introduced into the flow path L as the uncharged fine water having a particle size of 50 nanometers or less through the spout 13*c*1 which is the opening of the nanochannel 13*c* formed by the plurality of laminated particles 13, and discharging the fine water to the second space S2 together with the air introduced into the flow path L by the blower 120, and the discharge preparation control portion 152 which executes a discharge preparation mode of introducing the air in the first space S1 or the second space S2 into the flow path L by the blower 120 and non-electrifying the honeycomb member 131 (base material portion 11) by the electrifying portion 140 to adsorb the water introduced into the flow path L to the particles 13 through the nanochannel 13*c* from the spout 13*c*1.

In this case, the honeycomb member 131 (base material portion 11) is formed of a stainless-steel based metal, and the particles 13 are PEDOT/PSS including the core portion 13*a* formed of poly (3,4-ethylenedioxythiophene) and the shell portion 13*b* formed of poly (styrene sulfonic acid), and PEDOT/PSS is set so that a weight ratio of ethylenedioxythiophene (EDOT), which is a monomer of PEDOT, and PSS is between 1:4 and 1:6.

Further, in these cases, the fine water discharged into the second space S2 in the discharge mode is supplied to a human body existing in the second space S2.

Accordingly, the plurality of particles 13 are laminated as the film portion 12 on the outer surface of the honeycomb member 131 (base material portion 11) formed in a honeycomb shape to configure the fine water generating unit 130. When the plurality of particles 13 are laminated as the film portion 12, nanometer-sized nanochannels 13*c* are formed between the particles 13, more specifically, between the shell portions 13*b* of the particles 13. Since many polar functional groups 13*b*1 are distributed in this nanochannel 13*c*, the water adsorbed by the particles 13 in the adsorption state can be quickly moved toward the honeycomb member 131 (base material portion 11). Meanwhile, the adsorbed water quickly moves through the nanochannel 13*c* in the discharge state and is discharged into the air. In this case, since the nanochannel 13*c* is formed by a plurality of laminated particles 13, a large number of spouts 13*c*1 having a size of about 2 nanometers, which are openings for discharging the water corresponding to the nanochannel 13*c*, can exist. Accordingly, the particle size distribution of the water particles discharged from the fine water discharge device 100 can be aligned to be 50 nanometers or less.

Further, in the fine water discharge device 100, when the discharge control portion 151 executes the discharge mode, the electrifying portion 140 electrifies the honeycomb member 131 (base material portion 11). As a result, the temperatures of the particles 13 increase, and the fine water can be discharged. Therefore, the fine water discharge device 100 can discharge a large amount of uncharged fine water into the second space S2 without applying an electric charge to the fine water. Accordingly, the fine water discharged from the fine water discharge device 100 is uncharged and has a small particle size of 50 nanometers or less. Therefore, when the fine water is supplied to a human body existing in the second space S2, the fine water easily enters (infiltrates) a keratin of the human body. As a result, the fine water can infiltrate the inside of the keratin and can contribute satisfactorily to moisturizing of a skin or the like.

Further, in the fine water discharge device 100, the discharge preparation control portion 152 executes the discharge preparation mode so that the fine water generating unit 130 (more specifically, the particles 13) can adsorb the water of the air. Accordingly, in order to adsorb water and discharge the fine water, for example, it is not necessary to provide a water tank, a high-voltage power supply, an air guide tube, or the like, and it is possible to reduce a size of the fine water discharge device 100.

In this case, the discharge control portion 151 and the discharge preparation control portion 152 execute the cycle including the discharge mode and the discharge preparation mode a plurality of times.

According to this, for example, the discharge control portion 151 executes the discharge mode on the water which is adsorbed (moisture-absorbed) by the particles 13 of the honeycomb member 131 (base material portion 11) by the discharge preparation control portion 152 executing the discharge preparation mode, and thus, the fine water can be discharged to the second space S2. That is, by executing the cycle including the discharge mode and the discharge preparation mode, the water adsorbed (moisture-absorbed) from the air can be discharged as the fine water. Accordingly, it is not necessary to provide a water tank, a high-voltage power supply, an air guide tube, or the like, and it is possible to reduce the size of the fine water discharge device 100.

Further, since the cycle including the discharge mode and the discharge preparation mode can be executed a plurality of times, for example, the user of the fine water discharge device 100 can execute the cycle an arbitrary number of times. Therefore, the fine water discharge device 100 can be used according to the usage pattern of the user, and a convenience of the user can be improved.

Further, in these cases, in the discharge mode, the temperature of the electrified honeycomb member 131 (base material portion 11) increases by the range of 20° C. to 50° C. as compared with that of the non-electrified honeycomb material 131.

According to this, it is possible to reduce the thermal energy required when discharging the fine water into the second space S2 in the discharge mode. Meanwhile, in the discharge preparation mode, the honeycomb member 131 (base material portion 11) is in the non-electrified state. Therefore, less energy is required to operate the fine water discharge device 100, and as a result, energy saving can be achieved.

In these cases, the core portion 13*a* is formed of poly (3,4-ethylenedioxythiophene) out of a polymer material or an inorganic material. The shell portion 13*b* has, as the polar functional group 13*b*1, a sulfonic acid group ($-SO_3H$) which is at least one of a sulfonic acid group ($-SO_3H$), a carboxyl group ($-COOH$), a hydroxyl group ($-OH$), an amino group ($-NH_2$), an amid group ($-C{=}ONH-$), and a pyrrolidone group ($NCOC_3H_6$). In this case, the shell portion 13*b* is formed of, as the polymer material, polystyrene sulfonic acid (PSS) which is at least one of polystyrene sulfonic acid, polyvinyl sulfonic acid, polyvinyl pyrrolidone, polyvinyl alcohol, and sodium polyacrylate. Further, the honeycomb member 131 (base material portion 11) is formed of 20 chromium 5 aluminum-based ferritic stainless steel which is stainless steel which is at least one of a metal material such as a stainless-steel based metal or a copper-based metal, a carbon material, a conductive ceramic material, and a conductive resin material.

Accordingly, the particles 13 having a core-shell structure can have a large number of sulfonic acid groups ($-SO_3H$) in which the shell portion 13*b* formed of PSS is the polar functional group 13*b*1 capable of hydrogen bonding. Accordingly, the water contained in the air can be quickly and abundantly adsorbed in the adsorption state, and the adsorbed water can be quickly discharged to the air in the discharge state. As a result, the fine water discharge device 100 can discharge the fine water into the air while absorbing (adsorbing) the water from the air. Therefore, the fine water discharge device 100 can discharge the fine water by utilizing the water contained in the air.

First Modification Example

In the above embodiment, the particles 13 forming the film portion 12 have a core-shell structure formed of PEDOT/PSS, which is a conductive polymer material. That is, in the above embodiment, the core portion 13*a* of the particle 13 is formed of PEDOT, and the shell portion 13*b* of the particle 13 is formed of PSS.

Instead of this, it is possible to configure the particles 13 having a core-shell structure in which the core portion 13*a* of the particle 13 is formed of cerium oxide (CeO) which is an inorganic material and the shell portion 13*b* of the particle 13 is formed of polyvinylpyrrolidone, that is, PVP out of polystyrene sulfonic acid, polyvinylsulfonic acid, polyvinylpyrrolidone, polyvinyl alcohol, and sodium polyacrylate, which are polymer materials having the polar functional group 13*b*1 capable of hydrogen bonding. In this case, the PVP forming the shell portion 13*b* has a pyrrolidone group ($NCOC_3H_6$) out of a sulfonic acid group ($-SO_3H$), a carboxyl group ($-COOH$), a hydroxyl group ($-OH$), an amino group ($-NH_2$), an amide group ($-C{=}ONH-$), and the pyrrolidone group ($NCOC_3H_6$), which are the polar functional group 13*b*1 capable of hydrogen bonding.

As described above, even in a case where the particles 13 having the core-shell structure are formed of CeO/PVP and the film portion 12 containing the particles 13 is formed in a layer on the base material portion 11, when the base material portion 11 is in a non-electrified state, with the passage of time, the amount of water adsorbed by the particles 13 (shell portion 13*b*) increases and is stabilized in the state of the saturated water absorption rate. Further, in the fine water discharging element 10, the base material portion 11 is electrified and the temperatures of the particles 13 increase to be equal to or higher than a discharge temperature, and thus, the water adsorbed on the particles 13 (shell portion 13*b*) is discharged.

Then, even in the case of this first modification example, the shell portions 13*b* of the particles 13 are laminated in the film portion 12 in an aligned state as illustrated in FIG. 2. Further, the PVP constituting the shell portion 13*b* of the particles 13 has a large number of pyrrolidone groups ($NCOC_3H_6$) which are polar functional groups 13*b*1 capable of hydrogen bonding, and as illustrated in FIG. 3, has many pyrrolidone groups ($NCOC_3H_6$) around the shell portion 13*b*. Therefore, even in the film portion 12 of this first modification example, many pyrrolidone groups ($NCOC_3H_6$) are distributed in the nanochannel 13*c*, and the water contained in the air is adsorbed by hydrogen bonding on the pyrrolidone group ($NCOC_3H_6$) which is in contact with the air which is a fluid to be treated.

Accordingly, even in the fine water discharging element 10 of this first modification example, the water adsorbed on the surface of the film portion 12 moves at a high speed to the inside of the film portion 12 due to the difference in water concentration, and thus, a large amount of water can be adsorbed and retained from the air at a high speed. Further, since the water moves by using the difference in water concentration as the driving source in this way, when the amount of water inside the film portion 12 is large and the amount of water on the surface of the film portion 12 is small, that is, when air is dried, contrary to the above-mentioned adsorption, the water retained (adsorbed) on the surface of the film portion 12 moves from the inside of the film portion 12 at a high speed along the pyrrolidone group ($NCOC_3H_6$) existing in the nanochannel 13*c*. As a result, even in the fine water discharging element 10 of the first modification example, the water retained (adsorbed) inside the film portion 12 moves at a high speed to the surface of the film portion 12 due to the difference in water concentration, and thus, a large amount of water can be discharged to the air at a high speed. Therefore, even in this first modification example, the same effects as those of the above embodiment can be obtained.

Second Modification Example

Figure 13:
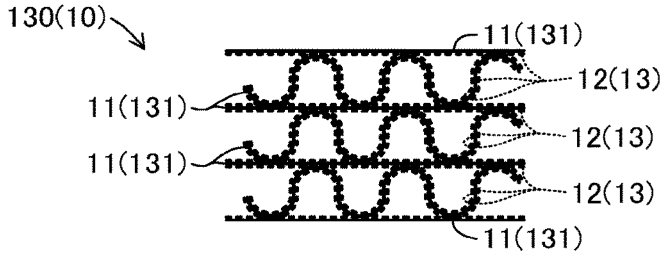
FIG. 13 is a cross-sectional view illustrating a first modification example of a fine water generating unit according to a second modification example of the embodiment.
Figure 14:
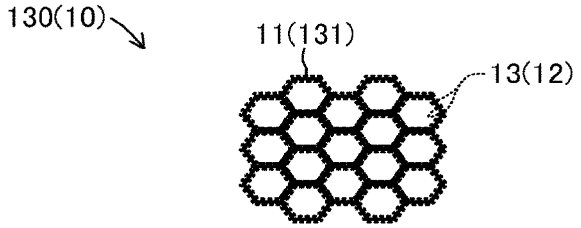
FIG. 14 is a cross-sectional view illustrating a second modification example of the fine water generating unit according to the second modification example of the embodiment.

In the above embodiment, the honeycomb shape of the honeycomb member 131 (base material portion 11) is triangular. Instead of this, the honeycomb shape of the honeycomb member 131 (base material portion 11) can be a wave shape (first modification example) as illustrated in FIG. 13 or a hexagonal shape (second modification example) as illustrated in FIG. 14. Even when the honeycomb shape is adopted for the honeycomb member 131 (base material portion 11), the particles 13 having a core-shell structure are applied to the surface of the honeycomb member 131 (base material portion 11) to form the film portion 12.

As a result, even in this case, in the fine water generating unit 130 (fine water discharging element 10), when the honeycomb member 131 (base material portion 11) is not electrified, the particles 13 having a core-shell structure constituting the film portion 12 can adsorb the water of the air introduced into the flow path L (adsorption state), and when the honeycomb member 131 (base material portion 11) is electrified, the water adsorbed by the particles 13 can be discharged as the fine water to the air introduced into the flow path L (discharge state). Therefore, the same effects as those of the above embodiment can be obtained.

Third Modification Example

Figure 15:
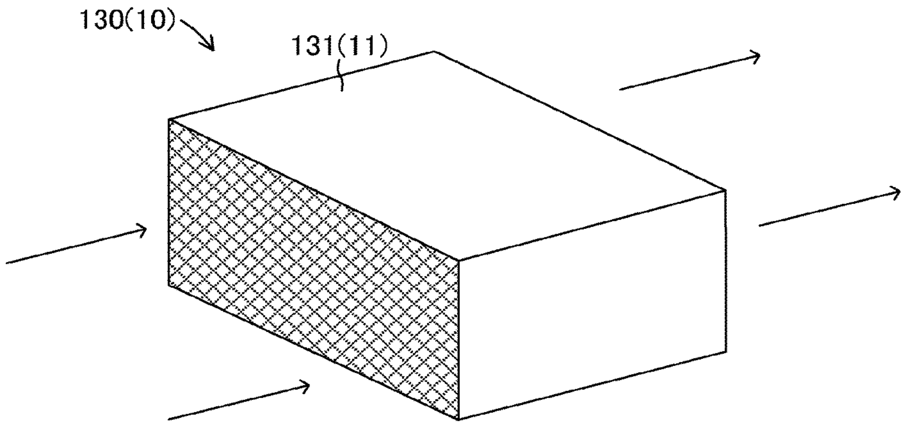
FIG. 15 is a perspective view illustrating a configuration of a fine water generating unit according to a third modification example of the embodiment.

In the above embodiment, the honeycomb member 131 (base material portion 11) has a columnar shape. Instead of this, as illustrated in FIG. 15, the honeycomb member 131 (base material portion 11) can be made prismatic. In this case, as for the honeycomb shape of the honeycomb member 131 (base material portion 11), the shapes of the first modification example illustrated in FIGS. 10 and 13 and the shape of the second modification example illustrated in FIG. 14 can be adopted.

Even when the prismatic honeycomb member 131 (base material portion 11) is adopted, the particles 13 having a core-shell structure are applied to the surface of the honeycomb member 131 (base material portion 11) to form the film portion 12. As a result, even in this case, in the fine water generating unit 130 (fine water discharging element 10), when the honeycomb member 131 (base material portion 11) is not electrified, the particles 13 having a core-shell structure constituting the film portion 12 can adsorb the water of the air introduced into the flow path L (adsorption state), and when the honeycomb member 131 (base material portion 11) is electrified, the water adsorbed by the particles 13 can be discharged as the fine water to the air introduced into the flow path L (discharge state). Therefore, the same effects as those of the above embodiment can be obtained.

Fourth Modification Example

Figure 16:
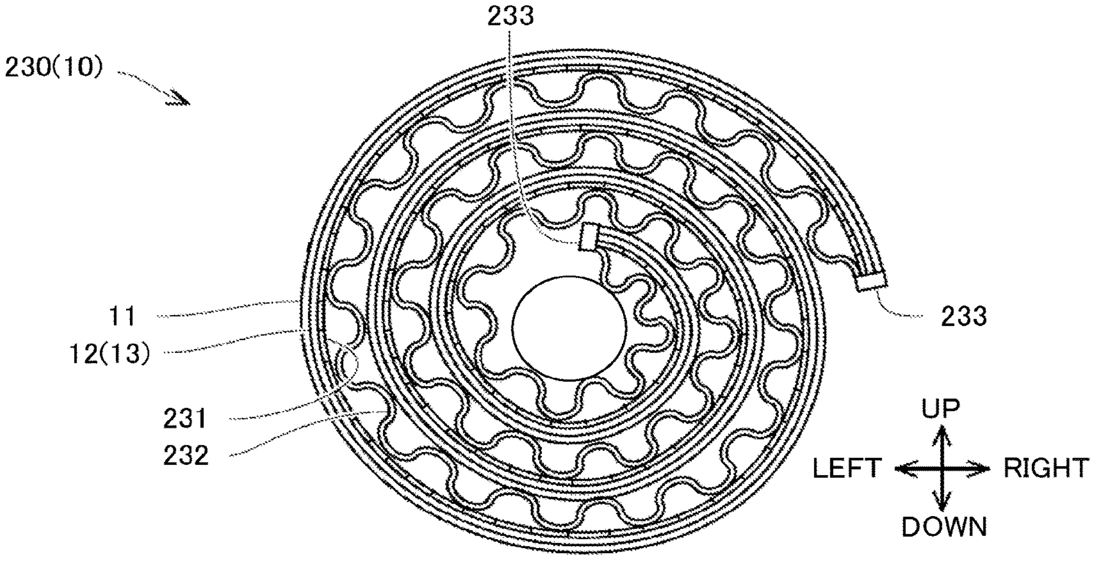
FIG. 16 is a plan view illustrating a configuration of a fine water generating unit according to a fourth modification example of the embodiment.

In the above embodiment, the fine water generating unit 130 includes the honeycomb member 131, and the base material portion 11 of the fine water discharging element 10 is integrally formed with the honeycomb member 131. Instead of this, it is also possible to provide a fine water generating unit 230 illustrated in FIG. 16. The fine water generating unit 230 includes the base material portion 11 formed in a spiral cross section using one fine water discharging element 10, and the particles 13 having a core-shell structure are applied to the outer surface (a surface corresponding to the inside of the spiral shape) of the base material portion 11 to form the film portion 12.

Figure 17:
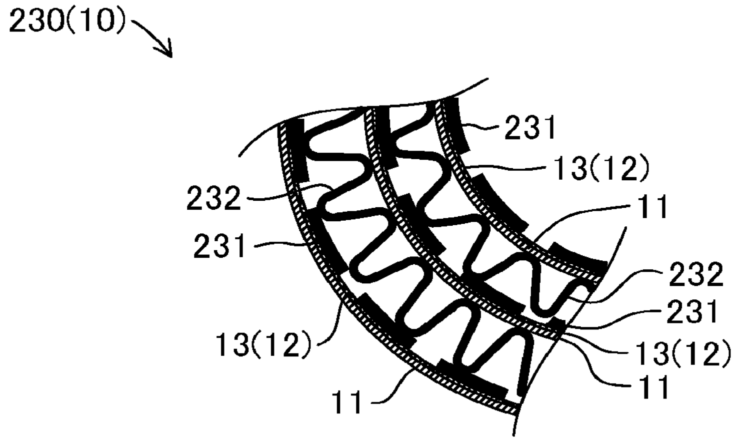
FIG. 17 is a cross-sectional view illustrating a detailed configuration of a fine water generating unit of FIG. 16.

In this case, the fine water generating unit 230 has a liner portion 231 and a corrugated portion 232 disposed on the surface side of the film portion 12. Each of the liner portion 231 and the corrugated portion 232 is provided in a spiral cross section. As illustrated in FIG. 17, the liner portion 231 is formed of a metal foil punching plate. The corrugated portion 232 is formed of pulp paper. Further, in this case, the fine water generating unit 230 includes electrodes 233 connected to the electrifying portion 140. The electrodes 233 are provided at both ends of the base material portion 11 of the fine water discharging element 10 constituting the fine water generating unit 230, respectively.

In the fine water generating unit 230 configured in this way, air flows through a gap formed between the corrugated portion 232 and the liner portion 231. Then, in the fine water generating unit 230 (fine water discharging element 10), when the base material portion 11 is not electrified, the particles 13 having a core-shell structure constituting the film portion 12 adsorb the water of the air introduced into the flow path L (adsorption state), and when the base material portion 11 is electrified, the water adsorbed by the particles 13 is discharged to the air introduced into the flow path L (discharge state). Moreover, when the base material portion 11 and the corrugated portion 232 are formed so as to be in contact with each other, the corrugated portion 232 is heated by heat generated when the base material portion 11 is electrified. Then, when the corrugated portion 232 is heated, the liner portion 231 is also heated, and as a result, the film portion 12 of the fine water discharging element 10, that is, the particles 13 are heated and quickly transitioned to the discharge state. Therefore, the same effects as those of the above embodiment can be obtained.

Figure 18:
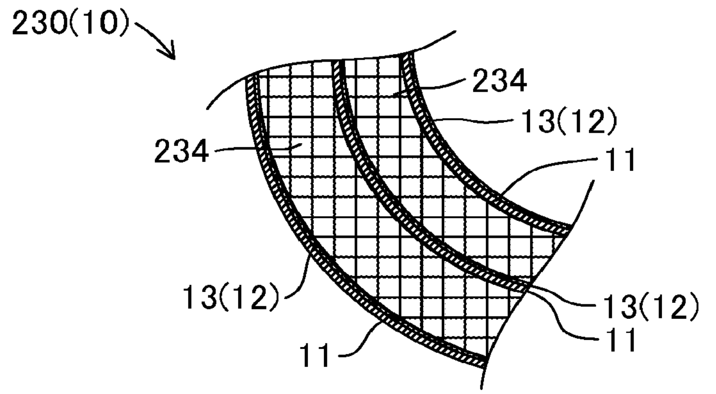
FIG. 18 is a cross-sectional view illustrating a first modification example of a fine water generating unit according to a fourth modification example of the embodiment.
Figure 19:
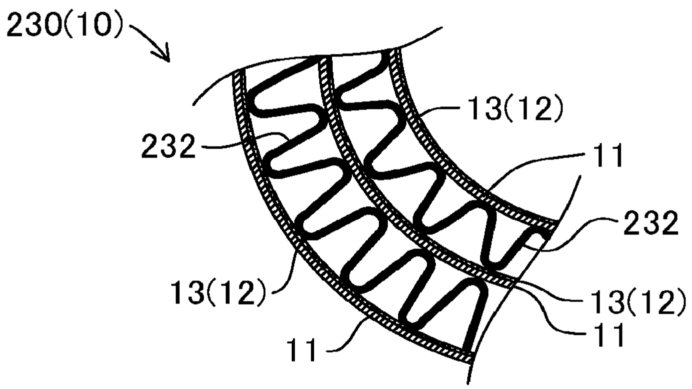
FIG. 19 is a cross-sectional view illustrating a second modification example of the fine water generating unit according to the fourth modification example of the embodiment.
Figure 20:
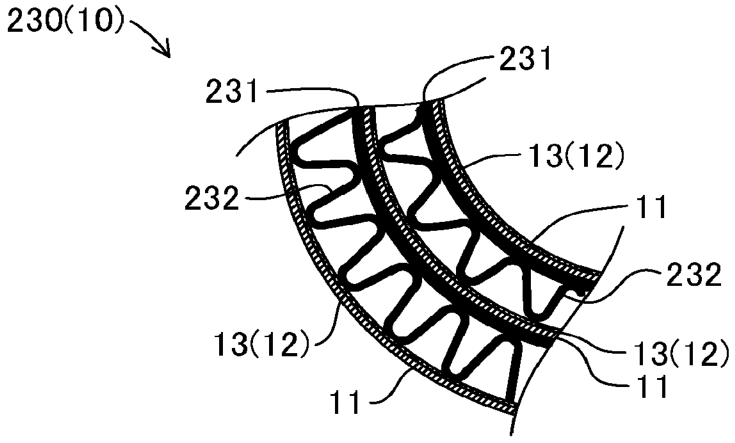
FIG. 20 is a cross-sectional view illustrating a third modification example of the fine water generating unit according to the fourth modification example of the embodiment.

Here, various changes can be made to the liner portion 231 and the corrugated portion 232 constituting the fine water generating unit 230. For example, as illustrated in FIG. 18 as a first modification example, the liner portion 231 can be omitted, and a metal mesh 234 can be formed instead of the corrugated portion 232. Further, as illustrated in FIG. 19 as a second modification example, the liner portion 231 can be omitted and the corrugated portion 232 can be formed of a metal plate. Further, as illustrated in FIG. 20 as a third modification example, the liner portion 231 can be formed of a metal plate and the liner portion 231 can be disposed between the base material portion 11 and the corrugated portion 232. Further, instead of the punching metal, the liner portion 231 can be formed of a metal mesh. Even when the liner portion 231 and the corrugated portion 232 are changed in this way, the same effects as those of the above embodiment can be obtained.

Fifth Modification Example

In the above-described embodiment and each of the above-described modification examples, the user directly operates the controller 150 which can be operated by the user to operate the fine water discharge device 100. In addition to this, for example, it is also possible to operate the fine water discharge device 100 by operating a mobile terminal (not illustrated) (specifically, for example, a smartphone or the like) possessed by the user. In this case, an application for selecting and instructing a control content, that is, an operation mode by the controller 150 is installed in the mobile terminal. Further, in this case, the fine water discharge device 100 includes a communication device 160 capable of communicating with the mobile terminal and communicating with the controller 150, as illustrated by a broken line in FIG. 1.

When the fine water discharge device 100 is operated by using the mobile terminal, the user selects the operation mode of the fine water discharge device 100 in the application activated in the mobile terminal, and thus, the selected operation mode is transmitted to the communication device 160 of the fine water discharge device 100. In the fine water discharge device 100, when the operation mode is received via the communication device 160, the controller 150 controls the operations of the blower 120 and the electrifying portion 140 according to the operation mode. As a result, the fine water discharge device 100 can be operated according to the operation mode selected by the user using the mobile terminal.

Meanwhile, the application installed on the mobile terminal can have a function of setting an arbitrary operation mode (aspect) in which the above-mentioned discharge mode and discharge preparation mode are combined with each other. Thereby, for example, the user can arbitrarily set a time at which the fine water is discharged, a wind speed by the blower 120, or the like.

In addition, for example, when a skin measurement application for measuring the amount of water in the skin or the like is installed on the mobile terminal, the fine water discharge device 100 can automatically set and operate an optimum operation mode according to a measurement result by the skin measurement application, that is, a skin condition of the user. In this case, the measurement result by the skin measurement application is transmitted to the controller 150 via the communication device 160. Accordingly, for example, when the water content of the skin of the user is small, the controller 150 sets a long time for discharging the fine water (that is, a time in the discharge mode), or sets a large number of times for discharging the fine water (that is, the number of times in the discharge mode). Therefore, the user does not need to set the time and the number of times by himself/herself, and can use the fine water discharge device 100 extremely easily and optimally.

Further, in this case, the communication device 160 can transmit data such as an operation content according to the skin measurement application of the fine water discharge device 100, specifically, the time or number of discharge modes according to the water content of the skin to an external server while ensuring confidentiality. Accordingly, by analyzing various data transmitted to the server and stored therein as big data, for example, an analysis result can be used for upgrading the skin measurement application, or for improving a control content of the fine water discharge device 100 by the controller 150. As a result, the user can operate and use the fine water discharge device 100 more finely according to his/her skin condition.

Sixth Modification Example

In the above-described embodiment and each of the above-described modification examples, the fine water discharge device 100 includes the fine water generating unit 130 (fine water discharging element 10) having the single honeycomb member 131, and the single honeycomb member 131 can be switched between the electrified state and the non-electrified state. Instead of this, the fine water discharge device 100 may include the fine water generating unit 130 (fine water discharging element 10) having a plurality of honeycomb members 131, and each honeycomb member 131 can be independently switched between the electrified state and the non-electrified state. Hereinafter, this sixth modification example will be specifically described.

Figure 21:
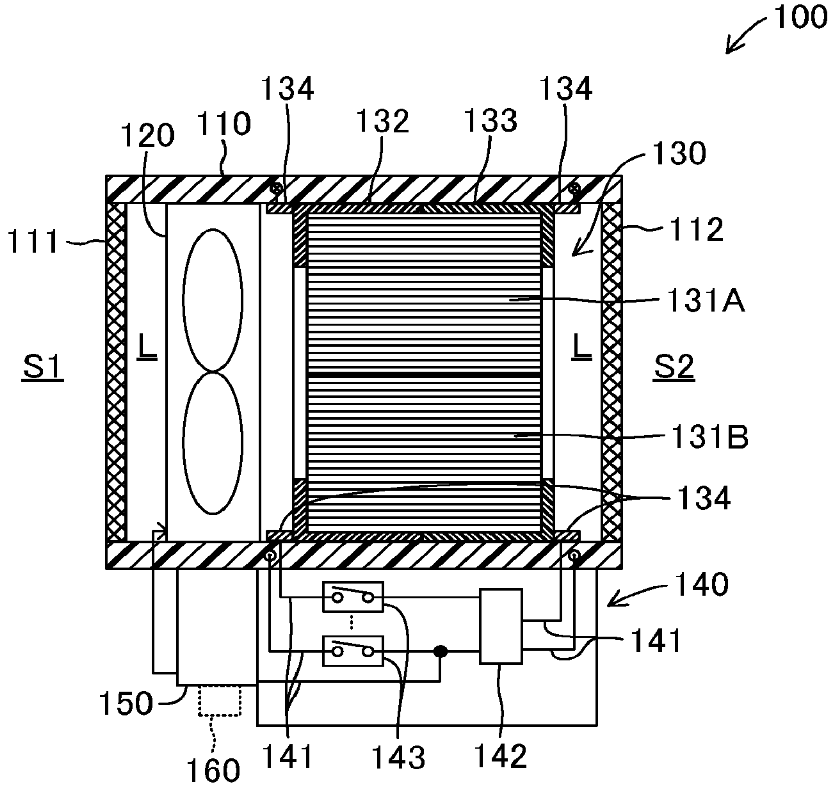
FIG. 21 is a cross-sectional view illustrating a configuration of a fine water discharge device according to a sixth modification example of the embodiment.

In the sixth modification example, for example, the fine water discharge device 100 includes two honeycomb members 131, as illustrated in FIG. 21. Moreover, in the following description, when the plurality of honeycomb members 131 are distinguished, the honeycomb members 131 are designated by reference numerals "A", "B", . . . . For example, when two honeycomb members 131 are distinguished, one honeycomb member 131 is referred to as a honeycomb member 131A, and the other honeycomb member 131 is referred to as a honeycomb member 131B.

The honeycomb member 131A and the honeycomb member 131B are independently switched between the electrified state and the non-electrified state, respectively, Therefore, as illustrated in FIG. 21, the electrodes 134 are electrically connected to the honeycomb member 131A and the honeycomb member 131B, respectively. Then, each electrode 134 is connected to each of the two switches 143, that is, provided corresponding to each electrode 134 via the electric wire 141. Here, in the electrifying portion 140, the switch 143, which matches the number of electrodes 134, in other words, the number of honeycomb members 131, is provided. For example, the electric wire 141 connected to the electrode 134 electrically connected to the honeycomb member 131A is accommodated inside a wall portion of the case 110.

The discharge control portion 151 of the controller 150 electrifies the honeycomb member 131A in the discharge mode to generate the fine water from the honeycomb member 131A. Meanwhile, the discharge preparation control portion 152 of the controller 150 non-electrifies the honeycomb member 131B and adsorbs the water of air to the honeycomb member 131B in the discharge preparation mode. Then, when a predetermined time elapses, the discharge control portion 151 electrifies the honeycomb member 131B and generates the fine water from the honeycomb member B in the discharge mode. Meanwhile, the discharge preparation control portion 152 non-electrifies the honeycomb member 131A and adsorbs the water of the air to the honeycomb member 131A in the discharge preparation mode. In this way, the discharge control portion 151 and the discharge preparation control portion 152 cooperate with each other, and the electrified states and the non-electrified states of the honeycomb member 131A and the honeycomb member 131B are switched repeatedly every time a predetermined time elapses. Accordingly, the fine water discharge device 100 can continuously discharge the fine water, and the same effects as those of the above embodiment can be obtained.

Figure 22:
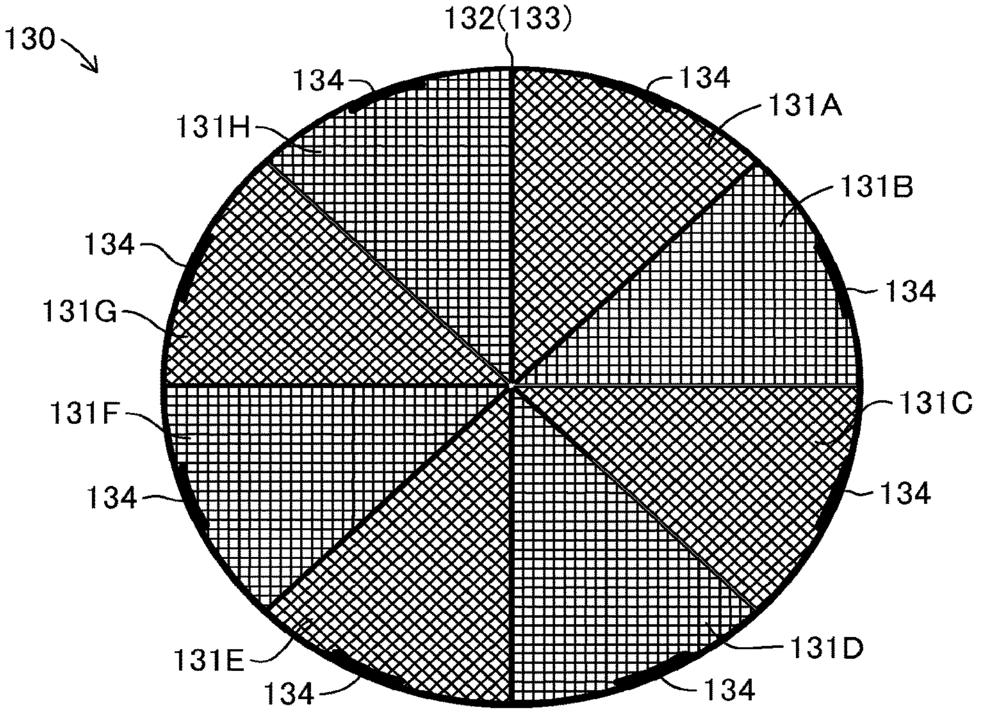
FIG. 22 is a plan view illustrating a configuration of a fine water generating unit according to a sixth modification example of the embodiment.
Figure 23:
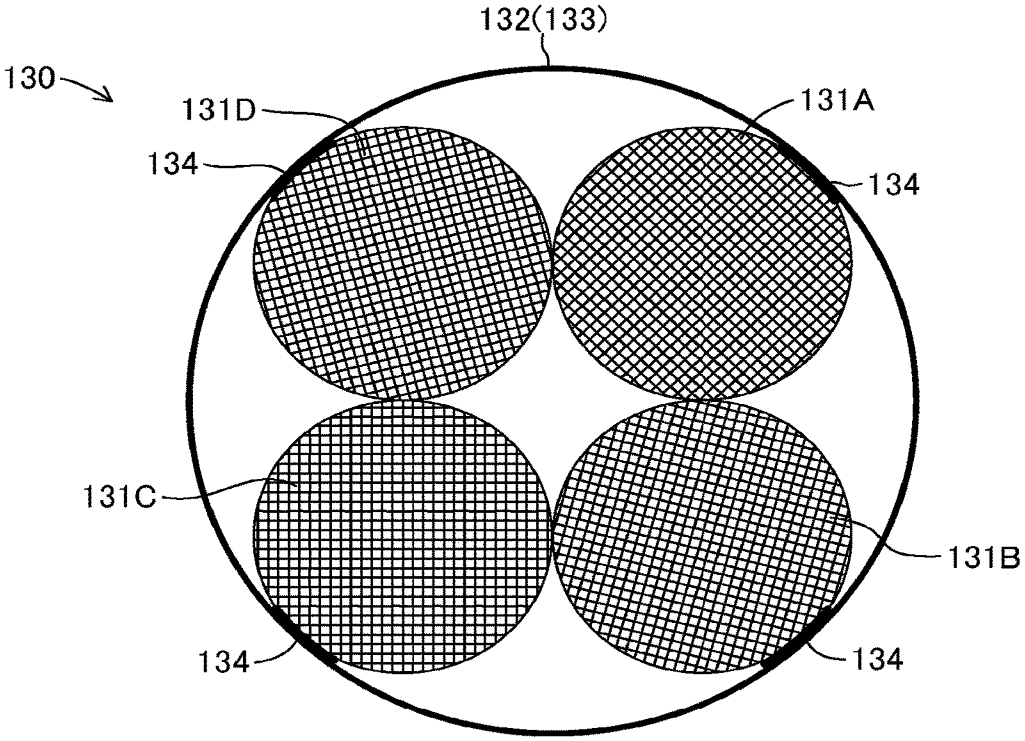
FIG. 23 is a plan view illustrating a configuration of a fine water generating unit according to a sixth modification example of the embodiment.

Here, the number (number of divisions) of the honeycomb members 131 is not limited to two as described above. For example, as illustrated in FIG. 22, it is also possible to provide honeycomb members 131A to 131H by executing division into eight in a circumferential direction. Further, for example, as illustrated in FIG. 23, it is also possible to provide four honeycomb members 131A to 131D having a diameter smaller than that of the case 110. In this way, when two or more honeycomb members 131 are provided, a ratio between the honeycomb member 131 in the electrified state and the honeycomb member 131 in the non-electrified state can be freely changed. Moreover, the shape of the divided honeycomb member 131 may be any shape as long as it can be accommodated inside the case 110, more specifically, as long as it can be accommodated in the first case member 132 and the second case member 133.

In the case illustrated in FIG. 22, the discharge control portion 151 and the discharge preparation control portion 152 cooperate with each other every time a predetermined time elapses, for example, the electrified states and the non-electrified states of the honeycomb member 131A, the honeycomb member 131C, the honeycomb member 131E, and the honeycomb member 131G can be switched repeatedly, and the non-electrified states and the electrified states of the honeycomb member 131B, the honeycomb member 131D, the honeycomb member 131F, and the honeycomb member 131H can be switched repeatedly. Accordingly, in the fine water discharge device 100, the ratios of the honeycomb member 131 in the electrified state and the honeycomb member 131 in the non-electrified state can be made equal to each other, and the fine water can be continuously discharged.

Similarly, in the case illustrated in FIG. 23, the discharge control portion 151 and the discharge preparation control portion 152 cooperate with each other every time a predetermined time elapses, for example, the non-electrified states and the electrified states of the honeycomb member 131A and the honeycomb member 131C can be switched repeatedly and the non-electrified states and the electrified states of the honeycomb member 131B and the honeycomb member 131D can be switched repeatedly. Accordingly, in the fine water discharge device 100, the ratios of the honeycomb member 131 in the electrified state and the honeycomb member 131 in the non-electrified state can be made equal to each other, and the fine water can be continuously discharged.

By the way, in particular, as illustrated in FIGS. 22 and 23, when the fine water discharge device 100 has three or more honeycomb members 131, as the ratio of the honeycomb member 131 in the electrified state and the honeycomb member 131 in the non-electrified state, for example, it is possible to increase the number of honeycomb members 131 which are not electrified as compared to the honeycomb members 131 which are electrified. In this case, the honeycomb member 131 in the non-electrified state increases the time for adsorbing the water in the air, and as a result, the amount of water adsorbed can increase. Therefore, when the honeycomb member 131 is switched to the electrified state, more fine water can be discharged, and the same effects as those of the above embodiment can be obtained.

Further, when the fine water discharge device 100 has a plurality of honeycomb members 131, the discharge control portion 151 and the discharge preparation control portion 152 can continuously switch between the electrified state and the non-electrified state so that the electrified state and the non-electrified state temporally overlap (wrap) each other between the respective honeycomb members 131. In this way, the amount of fine water generated by the fine water discharge device 100 can be made uniform by continuously switching between the electrified state and the non-electrified state so that the electrified state and the non-electrified state temporally overlap (wrap) each other, and the same effects as those of the above embodiment can be obtained.

The practice of the present invention is not limited to the above-described embodiment and each of the above-mentioned modification examples, and various modifications can be made without departing from the object of the present invention.

For example, in the above-described embodiment and each of the above-described modification examples, the base material portion 11 is formed of a conductive material. Instead of this, when the particles 13 have conductivity such as PEDOT/PSS, the base material portion 11 can be formed of a non-conductive material.

Further, in the above-described embodiment and each of the above-described modification examples, the fine water discharge device 100 is configured to integrally include the blower 120. However, it is also possible to configure the fine water discharge device 100 to include the blower 120 as a separate body. In this case, the fine water discharge device 100 excluding the blower 120 can be attached to a device having a blower function, for example, a dryer, an air conditioner, a fan, or the like. As a result, the controller 150 of the fine water discharge device 100 electrifies or does not electrify the fine water generating unit 130 (nano-sized water particle discharge element 10) in accordance with the fact that the device having the blower function blows air, and thus, the fine water discharge device 100 can discharge fine water or adsorb water. Therefore, even in this case, the same effects as those of the above-described embodiment and the above-described modification examples can be expected.

Further, in the above-described embodiment and each of the above-described modification examples, the discharge preparation control portion 152 constituting the controller 150 executes the discharge preparation mode, and thus, the fine water generating unit 130 (nano-sized water particle discharge element 10) adsorbs (moisture-adsorbs) the water in the air introduced into the flow path L of the case 110. Instead of or in addition to this, for example, inside the case 110, a sheet member moistened with water can be disposed to be interposed between the blower 120 and the fine water generating unit 130 (honeycomb member 131, first case member 132, and second case member 133) inside the flow path L. Alternatively, inside the case 110, a spray mechanism for spraying vapor-like (mist-like) water can be disposed inside the flow path L between the blower 120 and the fine water generating unit 130.

When the sheet member or the spray mechanism is disposed in this way, in the discharge preparation mode, unlike the case of the above embodiment, the discharge preparation control portion 152 rotationally drives the blower 120 in the first direction to flow air from the first space S1 side to the second space S2 side in the flow path L. Accordingly, the water contained in the sheet member or the water sprayed from the spray mechanism is contained in the air and supplied to the fine water generating unit 130 (nano-sized water particle discharge element 10). Therefore, the sheet member or the spray mechanism can effectively assist the film portion 12 (particles 13) cooled in the non-electrified state adsorbing (moisture-absorbing) water (water clusters).

Further, in the above-described embodiment and each of the above-described modification examples, the fine water discharge device 100 discharges only fine water into the second space S2. In addition to this, the fine water discharge device 100 can be configured to discharge steam-like water or chemicals at the same time as the fine water. In this case, for example, the fine water discharge device 100 can include a steam generator having a tank for storing water or chemicals. As a result, as described above, at the same time that the fine water discharge device 100 discharges fine water, the steam generator can steam the water or the chemicals and discharge the steamed water or chemicals to the second space S2.

Further, in the above-described embodiment and each of the above-described modification examples, the fine water generating unit 130 is configured so that the film portion 12 (particles 13) is provided on the entire honeycomb member 131. Instead of this, for example, a through hole is provided in the central portion of the honeycomb member 131, a fragrance agent such as aroma oil can be stored in the through hole. In this case, the discharge control portion 151 executes the discharge mode to increase the temperature of the honeycomb member 131 (base material portion 11) in the electrified state. Accordingly, as described above, the fine water can be discharged into the second space S2, the stored fragrance agent can be evaporated, and a fragrance component can also be discharged into the second space S2.

Further, in the above-described embodiment and each of the above-described modification examples, the fine water discharge device 100 is configured to include one blower 120 and one fine water generating unit 130 inside the case 110. Instead of this, it is also possible to configure the fine water discharge device 100 to include a plurality of the blowers 120 and a plurality of the fine water generating units 130 inside the case 110. In this case, for example, a plurality of pairs consisting of the blowers 120 and the fine water generating units 130 can be provided in parallel in a direction orthogonal to an axial direction of the case 110, or the plurality of pairs can be provided in series along the axial direction of the case 110.

Accordingly, each pair (blower 120 and fine water generating unit 130) can be operated in a sequence or at the same time. Therefore, in this case, a discharge amount or a discharge distance of the fine water discharged into the second space S2 can be adjusted, or a discharge time when the fine water is continuously discharged can be adjusted.

Further, in the above-described embodiment and each of the above-described modification examples, when the controller 150 generates fine water and discharges the fine water, the controller 150 closes the switch 143 of the electrifying portion 140 to operate the blower 120 and electrify the fine water generating unit 130. Meanwhile, when the controller 150 stops the generation and discharge of the fine water, the controller 150 opens the switch 143 of the electrifying portion 140 to stop the operation of the blower 120 and non-electrify the fine water generating unit 130.

Instead of this, for example, in a configuration in which the electrification to the blower 120 can be maintained and the operation of the blower 120 can be continued, when the fine water is discharged and stopped, the controller 150 controls the switch 143 of the electrifying portion 140 so that the switch 143 is closed or opened, and switches the fine water generating unit 130 between the electrified state and the non-electrified state to discharge and stop the fine water.

Further, in the above-described embodiment and each of the above-described modification examples, the fine water discharge device 100 discharges the fine water formed of the water cluster by the fine water generating unit 130 (nano-sized water particle discharge element 10) into the second space S2 as it is. In addition to this, for example, a device for converting the water cluster into plasma, for example, corona discharge, creeping discharge, or the like, which is well-known low-temperature plasma generation means, is provided, and thus, active oxygen (OH-radical) having strong oxidizing power can also be generated efficiently from water cluster (fine water). As described above, the active oxygen (OH-radical) generated from the water cluster (fine water) has strong oxidizing power. For example, when the fine water discharge device 100 (nano-sized water particle discharge element 10) is applied to an air purifier, it can be effective in sterilizing bacteria, preventing insects, and preventing mold.

Further, in the above-described embodiment and each of the above-described modification examples, the power supply 142 of the electrifying portion 140 is assumed to be a commercial power supply. Therefore, the fine water discharge device 100 of the above-described embodiment and each of the above-described modification examples is a stationary type device. Instead of this, by using a battery capable of charging and discharging as the power supply 142, the fine water discharge device 100 can be made portable (so-called cordless type device).

Further, in the above-described embodiment and each of the above-described modification examples, the user directly operates the controller 150 of the fine water discharge device 100. Instead of or in addition to this, for example, the user can operate a remote controller which enables a remote control of the controller 150, or set a timer for an operation time and a stop time of the controller 150 so as to operate the fine water discharge device 100. Alternatively, when the fine water discharge device 100 includes a motion sensor, a temperature/humidity sensor, or the like, the controller 150 can operate the fine water discharge device 100 according to detection results of these sensors.

Further, in the above-described embodiment and each of the above-described modification examples, the fine water discharge device 100 is applied to the beauty equipment so that the fine water can effectively infiltrate the skin of the user. As described above, the fine water generated and discharged by the fine water discharge device 100 (nano-sized water particle discharge element 10) is the bound water which has the particle size of 50 nanometers or less and is uncharged (non-electrified). Therefore, the fine water discharge device 100 can be applied to other than the beauty equipment.

For example, when the fine water discharge device 100 (nano-sized water particle discharge element 10) is applied to a dryer to discharge the fine water to a scalp or hair of the user, the fine water can infiltrate the scalp or hair and apply a moisturizing effect to the scalp or hair. As a result, for example, improvement of hair gloss, prevention of itchiness, prevention of dandruff, prevention of hair loss, or the like can be expected. Further, when the fine water discharge device 100 (nano-sized water particle discharge element 10) is applied to a hair growth promoter, infiltration of a hair growth agent applied to the scalp of the user can be promoted, and the promotion of hair growth can be expected.

Further, when the fine water discharge device 100 (nano-sized water particle discharge element 10) is applied to a drug delivery device to discharge the fine water to a skin to which the drug is applied, a percutaneous absorption of the drug can be promoted, and for example, improvement in effects of a drug with respect to various diseases can be expected. Further, when the fine water discharge device 100 (nano-sized water particle discharge element 10) is applied to a dry eye prevention device (eye mask or the like) to discharge the fine water to eyes or a face of the user, it can be expected that the infiltration of fine water suppresses dry of the eyes. Further, when the fine water discharge device 100 (nano-sized water particle discharge element 10) is applied to an inhaler or a respirator to discharge the fine water to a mucous membrane or the like in an oral cavity of the user, it is expected that a moisturizing effect and a humidifying effect will be improved by the infiltration of the fine water into the mucous membrane or the like.

Further, in these cases, the fine water generated by the fine water discharge device 100 (nano-sized water particle discharge element 10) is directly discharged to the user (human). Instead of this, it is also possible to discharge the fine water generated by the fine water discharge device 100 (nano-sized water particle discharge element 10) to a non-human object. For example, when the fine water discharge device 100 (nano-sized water particle discharge element 10) is applied to a refrigerator or a pantry to discharge the fine water into food, since the fine water is uncharged (non-electrified) bound water, a moisturizing effect of stored food can be enhanced. As a result, for example, it can be expected to maintain a freshness of the food refrigerated in the refrigerator and improve flavor of the food stored in the pantry.

Further, when the fine water discharge device 100 (nano-sized water particle discharge element 10) is applied to a plant growing device to discharge the fine water to a plant, for example, it can be expected to promote a growth of the seedling by discharging the fine water to the seedling. Further, when the fine water discharge device 100 (nano-sized water particle discharge element 10) is applied to a static eliminator to discharge the fine water to an industrial product or the like, since the fine water is uncharged (non-electrified), for example, it can be expected to have an effect of removing static electricity from paper, a semiconductor, a paint, or the like.

REFERENCE SIGNS LIST

10: fine water discharging element, 11: base material portion, 12: conductive polymer film portion, 13: particles, 13*a*: core portion, 13*b*: shell portion, 13*c*: nanochannel (channel), 13*c*1: spout (opening), 100: fine water discharge device, 110: case, 120: blower (air blowing unit), 130: fine water generating unit, 131: honeycomb member (base material portion), 132: first case member, 133: second case member, 134: electrode, 140: electrifying portion, 141: electric wire, 142: power supply, 143: switch, 150: controller (control portion), 151: discharge control portion, 152: discharge preparation control portion, 160: communication device, 230: fine water generating unit, 231: liner portion, 232: corrugated portion, 233: electrode, L: flow path, S1: first space, S2: second space

The invention claimed is:

1. A fine water discharge device comprising:

a case which has a flow path allowing a first space and a second space to communicate with each other;

an air blowing unit which is disposed in the flow path, introduces air in the first space into the flow path, and discharges the air introduced into the flow path into the second space;

a fine water generating unit which is disposed in the flow path, includes a base material portion and a plurality of particles having a core-shell structure including a core portion forming a nucleus and a shell portion formed of a polymer material having a polar functional group capable of hydrogen bonding to cover the core portion, and in which at least one of the base material portion and the plurality of particles has conductivity, the plurality of particles are laminated in a film shape on an outer surface of the base material portion to form a film portion having nanometer-sized channels smaller in width than said particles, formed between the shell portions of the plurality of particles and distributed over the film portion, and states of the plurality of particles of the film portion are transitioned between an adsorption state where water is adsorbed and a discharge state where the adsorbed water is discharged to the air to generate fine water;

an electrifying portion electrically connected to the base material portion of the fine water generating unit to electrify the base material portion; and a control portion which controls the air blowing unit and the electrifying portion, wherein the control portion includes:

a discharge control portion which executes a discharge mode of introducing the air in the first space into the flow path by the air blowing unit, electrifying the base material portion of the fine water generating unit by the electrifying portion to have the base material portion to be in an electrified state by increasing temperature of the film portion under a state that the base material portion generates heat to discharge the water adsorbed on the plurality of particles of the fine water generating unit to the air introduced into the flow path as uncharged fine water having a particle size of 50 nanometers or less through an opening of the channels formed by the plurality of particles, and discharging the fine water to the second space together with the air introduced into the flow path by the air blowing unit, and a discharge preparation control portion which executes a discharge preparation mode of introducing the air in the first space or the second space into the flow path by the air blowing unit and non-electrifying the base material portion by the electrifying portion to have the base material portion to be in a non-electrified state by decreasing the temperature of the film portion compared to the temperature under the electrified state of the base material portion, under a state that the base material portion does not generate heat to adsorb the water introduced into the flow path to the plurality of particles through the channels from the opening.

2. The fine water discharge device according to claim 1, wherein the discharge control portion and the discharge preparation control portion execute a cycle including the discharge mode and the discharge preparation mode a plurality of times.

3. The fine water discharge device according to claim 1, wherein in the discharge mode, a temperature of the electrified base material portion increases by a range of 20° C. to 50° C. as compared with that of the non-electrified base material portion.

4. The fine water discharge device according to claim 1, wherein in the discharge mode, the fine water discharged into the second space is supplied to a human body existing in the second space.

5. The fine water discharge device according to claim 1, wherein the base material portion is formed of stainless-steel based metal, and the plurality of particles are PEDOT/PSS constituted by the core portion formed of poly (3,4-ethylenedioxythiophene) and the shell portion formed of poly (styrene sulfonic acid).

6. The fine water discharge device according to claim 5, wherein the PEDOT/PSS is set so that a weight ratio between ethylenedioxythiophene (EDOT) which is a monomer of the PEDOT and the poly (styrene sulfonic acid) is between 1:4 and 1:6.

7. A fine water discharge device comprising:

a case which has a flow path allowing a first space and a second space to communicate with each other;

an air blowing unit which is disposed in the flow path, introduces air in the first space into the flow path, and discharges the air introduced into the flow path into the second space;

a fine water generating unit which is disposed in the flow path, includes a base material portion and a plurality of particles having a core-shell structure including a core portion forming a nucleus and a shell portion formed of a polymer material having a polar functional group capable of hydrogen bonding to cover the core portion, and in which at least one of the base material portion and the plurality of particles has conductivity, the plurality of particles are laminated in a film shape on an outer surface of the base material portion to form a film portion having a channel formed between the shell portions of the plurality of particles and being smaller than a diameter of the particles, and states of the plurality of particles of the film portion are transitioned between an adsorption state where water is adsorbed and a discharge state where the adsorbed water is discharged to the air to generate fine water;

an electrifying portion electrically connected to the base material portion of the fine water generating unit to electrify the base material portion; and a control portion which controls the air blowing unit and the electrifying portion, wherein the control portion includes:

a discharge control portion which executes a discharge mode of introducing the air in the first space into the flow path by the air blowing unit, electrifying the base material portion of the fine water generating unit by the electrifying portion to have the base material portion to be in an electrified state by increasing temperature of the film portion under a state that the base material portion generates heat to discharge the water adsorbed on the plurality of particles of the fine water generating unit to the air introduced into the flow path as uncharged fine water having a particle size of 50 nanometers or less through an opening of the channel formed by the plurality of particles, and discharging the fine water to the second space together with the air introduced into the flow path by the air blowing unit, wherein in the discharge mode, a temperature of the electrified base material portion increases by a range of 20° C. to 50° C. as compared with that of the non-electrified base material portion, and a discharge preparation control portion which executes a discharge preparation mode of introducing the air in the first space or the second space into the flow path by the air blowing unit and non-electrifying the base material portion by the electrifying portion to have the base material portion to be in a non-electrified state by decreasing the temperature of the film portion compared to the temperature under the electrified state of the base material portion, under a state that the base material portion does not generate heat to adsorb the water introduced into the flow path to the plurality of particles through the channel from the opening.

8. The fine water discharge device according to claim 7, wherein the discharge control portion and the discharge preparation control portion execute a cycle including the discharge mode and the discharge preparation mode a plurality of times.

9. The fine water discharge device according to claim 7, wherein in the discharge mode, the fine water discharged into the second space is supplied to a human body existing in the second space.

10. The fine water discharge device according to claim 7, wherein the base material portion is formed of stainless-steel based metal, and the plurality of particles are PEDOT/PSS constituted by the core portion formed of poly (3,4-ethylenedioxythiophene) and the shell portion formed of poly (styrene sulfonic acid).

11. The fine water discharge device according to claim 10, wherein the PEDOT/PSS is set so that a weight ratio between ethylenedioxythiophene (EDOT) which is a monomer of the PEDOT and the poly (styrene sulfonic acid) is between 1:4 and 1:6.

* * * * *